United States Patent
Yanagida et al.

(10) Patent No.: US 11,125,740 B2
(45) Date of Patent: Sep. 21, 2021

(54) METHOD FOR MEASURING IMMUNOSTIMULATORY RESPONSE OF IMMUNE CELL, METHOD FOR DETERMINING ABILITY TO FORM IMMUNE SYNAPSE IN IMMUNE CELL, AND CELL ANALYZER

(71) Applicant: SYSMEX CORPORATION, Kobe (JP)

(72) Inventors: Masatoshi Yanagida, Hyogo (JP); Keiko Miwa, Hyogo (JP); Yuma Oka, Hyogo (JP)

(73) Assignee: SYSMEX CORPORATION, Kobe (JP)

(*) Notice: Subject to any disclaimer, the term of this patent is extended or adjusted under 35 U.S.C. 154(b) by 305 days.

(21) Appl. No.: 15/949,577

(22) Filed: Apr. 10, 2018

(65) Prior Publication Data
US 2018/0292385 A1    Oct. 11, 2018

(30) Foreign Application Priority Data
Apr. 11, 2017 (JP) ................. JP2017-078407

(51) Int. Cl.
*G01N 33/50* (2006.01)
*G01N 33/58* (2006.01)
(Continued)

(52) U.S. Cl.
CPC ......... *G01N 33/505* (2013.01); *G01N 15/147* (2013.01); *G01N 15/1434* (2013.01);
(Continued)

(58) Field of Classification Search
CPC ............ G01N 33/505; G01N 33/5058; G01N 33/582; G01N 15/1434; G01N 15/147;
(Continued)

(56) References Cited

U.S. PATENT DOCUMENTS

| | | | |
|---|---|---|---|
| 2013/0020498 A1 | 1/2013 | Ebi et al. | |
| 2015/0038363 A1* | 2/2015 | Kishi | C12N 5/0636 506/9 |

FOREIGN PATENT DOCUMENTS

| | | |
|---|---|---|
| EP | 2 045 595 A2 | 4/2009 |
| EP | 2 045 595 A3 | 5/2013 |

(Continued)

OTHER PUBLICATIONS

Hosseini et al. Immune synapse formation determines interaction forces between T cells and antigen-presenting cells measured by atomic force microscopy. PNAS 106 (42): 17852-17857 Oct. 2009.*

(Continued)

*Primary Examiner* — Gailene Gabel
(74) *Attorney, Agent, or Firm* — Sughrue Mion, PLLC

(57) ABSTRACT

Disclosed is a method for measuring an immunostimulatory response of an immune cell, including (i) bringing a measurement target immune cell into contact with an immunostimulator, (ii) forming a contact surface with a substance different from the measurement target immune cell on the measurement target immune cell, (iii) bringing the measurement target immune cell into contact with a capturing body that binds to a surface antigen on the contact surface and is capable of generating an optical signal, (iv) detecting the optical signal generated from the capturing body, and (v) determining whether or not the measurement target immune cell from which the contact surface has been eliminated before detecting the optical signal has an immunostimulatory response, based on the detected optical signal.

19 Claims, 23 Drawing Sheets

(51) Int. Cl.
*G06T 7/00* (2017.01)
*G01N 15/14* (2006.01)
*G01N 33/49* (2006.01)
*G01N 15/10* (2006.01)

(52) U.S. Cl.
CPC ..... *G01N 15/1475* (2013.01); *G01N 33/4915* (2013.01); *G01N 33/5058* (2013.01); *G01N 33/582* (2013.01); *G06T 7/0012* (2013.01); *G01N 2015/1006* (2013.01); *G01N 2015/1497* (2013.01); *G06T 2207/10064* (2013.01); *G06T 2207/30024* (2013.01)

(58) Field of Classification Search
CPC ........... G01N 15/1475; G01N 33/5047; G01N 33/4915; G06T 7/0012
See application file for complete search history.

(56) References Cited

FOREIGN PATENT DOCUMENTS

| | | |
|---|---|---|
| EP | 2 824 182 A1 | 1/2015 |
| JP | 2007-104944 A | 4/2007 |

OTHER PUBLICATIONS

Leo M. Carlin et al., "Secretion of IFN-γ and not IL-2 by anergic human T cells correlates with assembly of an immature immune synapse," Blood, Dec. 1, 2005, pp. 3874-3879, vol. 106, No. 12.
Tadashi Yokosuka et al., "Spatiotemporal Regulation of T Cell Costimulation by TCR-CD28 Microclusters and Protein Kinase C ⊖ Translocation," Immunity, Oct. 17, 2008, pp. 589-601, vol. 29.
Babak H. Hosseini et al., "Immune synapse formation determines interaction forces between T cells and antigen-presenting cells measured by atomic force microscopy," PNAS, Oct. 20, 2009, pp. 17852-17857, vol. 106, No. 42.
The Japanese Office Action dated Jan. 4, 2021 in a counterpart Japanese patent application No. 2017-078407.
Emre Balta et al.: "Qualitative and quantitative analysis of PMN/T-cell interactions by InFlow and super-resolution microscopy", Methods, vol. 112, pp. 25-38, Elsevier, 2017.
Sarah E. Headland et al May 1, 2015: "Cutting-Edge Analysis of Extracellular Microparticles using ImagStreamxImaging Flow Cytometry", Scientific Reports, vol. 4, Article No. 5237, May 1, 2015, 10 pages.
The Communication pursuant to Article 94(3) EPC dated May 26, 2021 in a counterpart European patent application No. 18166512.6.
The Japanese Office Action dated Jul. 13, 2021 in a counterpart Japanese patent application No. 2017-078407.

* cited by examiner

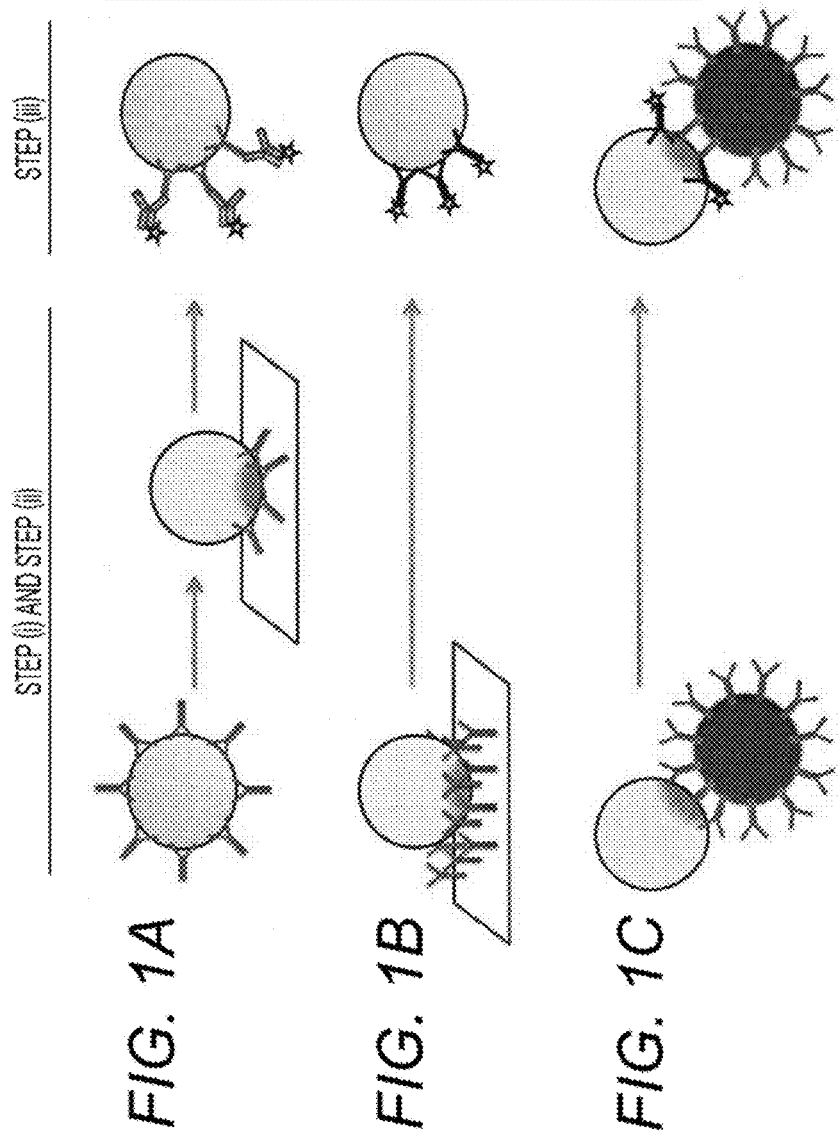
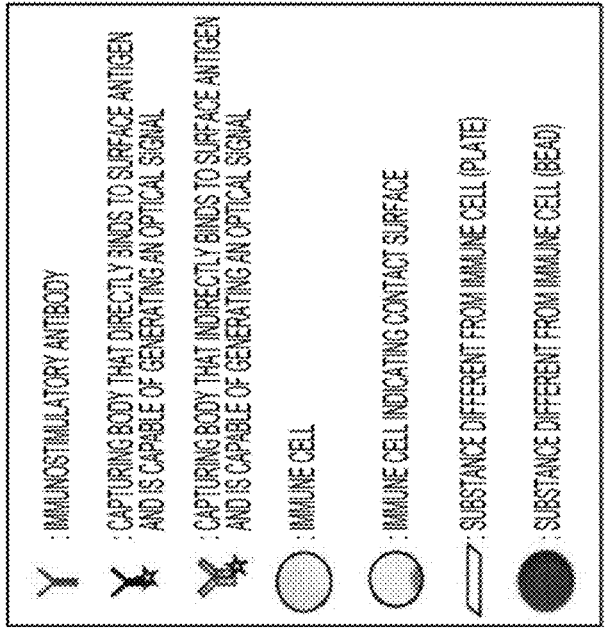
FIG. 1A
FIG. 1B
FIG. 1C

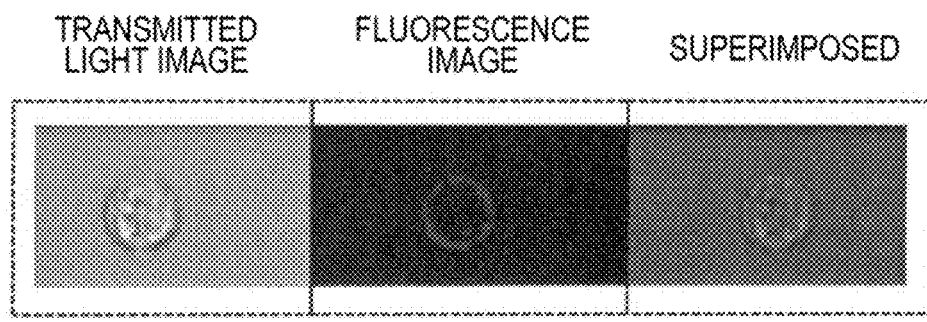
FIG. 8A
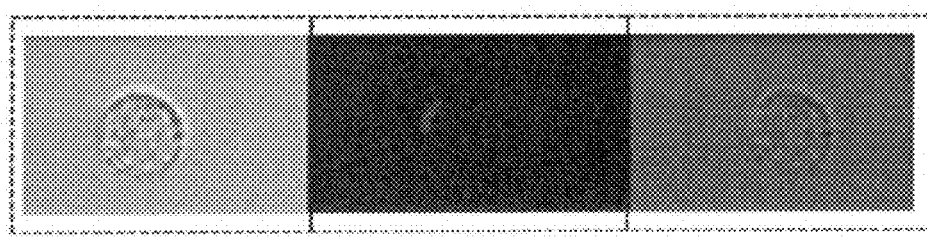
FIG. 8B
FIG. 9
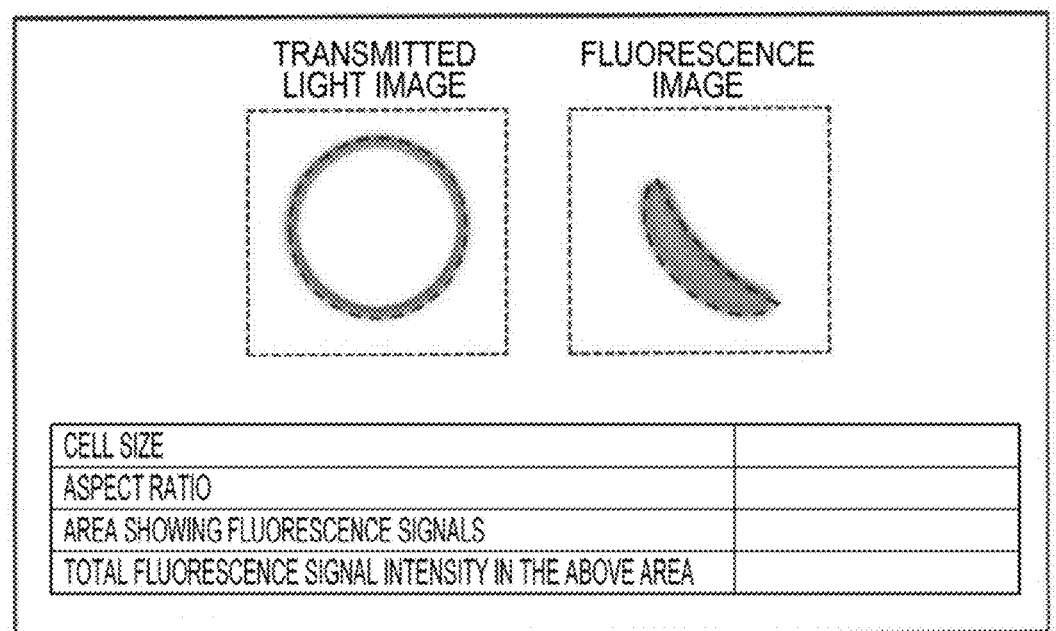

CELL

WITHOUT IMMUNE STIMULATION
DIC    CD28    Merge

WITH IMMUNE STIMULATION
DIC    CD28    Merge

WITHOUT IMMUNE STIMULATION

WITH IMMUNE STIMULATION

FIG. 17A CD3 — WITHOUT IMMUNE STIMULATION
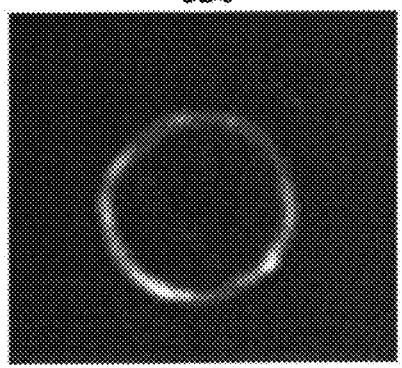
FIG. 17C CD40L — WITHOUT IMMUNE STIMULATION
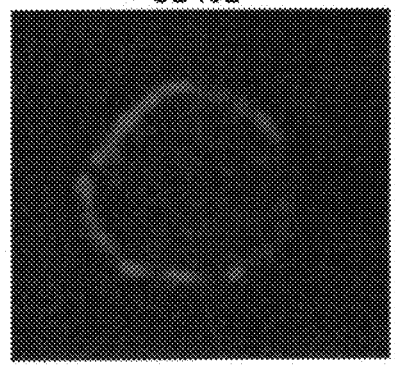
FIG. 17B CD3 — WITH IMMUNE STIMULATION
FIG. 17D CD40L — WITH IMMUNE STIMULATION
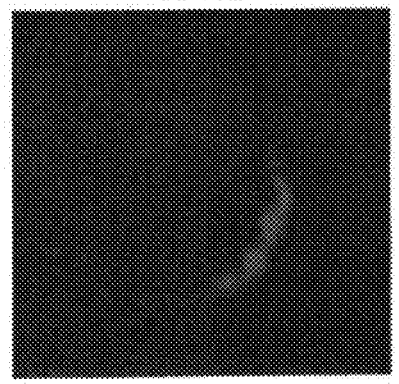

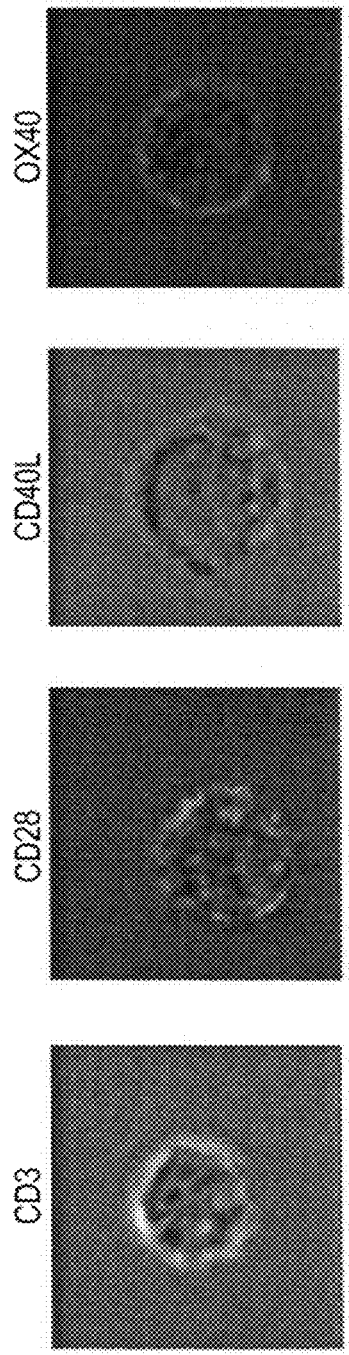
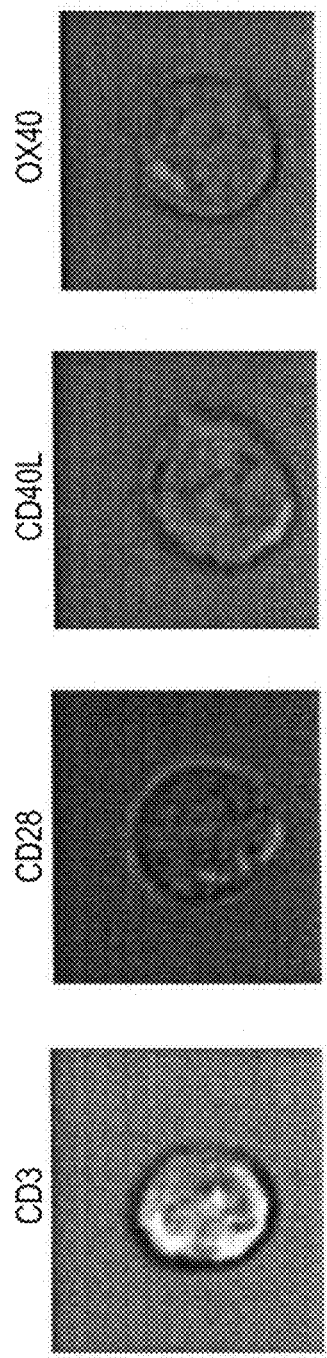

WITHOUT IMMUNE STIMULATION

WITH IMMUNE STIMULATION

WITHOUT IMMUNE STIMULATION

WITH IMMUNE STIMULATION

METHOD FOR MEASURING IMMUNOSTIMULATORY RESPONSE OF IMMUNE CELL, METHOD FOR DETERMINING ABILITY TO FORM IMMUNE SYNAPSE IN IMMUNE CELL, AND CELL ANALYZER

CROSS REFERENCE TO RELATED APPLICATIONS

This application claims priority from prior Japanese Patent Application No. 2017-078407, filed on Apr. 11, 2017, entitled "Method for measuring immunostimulatory response of immune cell, method for determining ability to form immune synapse in immune cell, and cell analyzer", the entire contents of which are incorporated herein by reference.

TECHNICAL FIELD

The present invention relates to a method for measuring an immunostimulatory response of an immune cell, a method for determining ability to form an immune synapse in an immune cell, and a cell analyzer.

BACKGROUND

Immunization is a generic term for cellular and humoral biological reactions in which a living organism performs to discriminate self and non-self in the body and exclude non-self. The immune system is a very important physiological mechanism in life activities. Cells of the immune system are involved in the activation and suppression of the immune system, by secreting proteins called cytokines or exerting cytotoxic functions.

The immune system is deeply involved in the rejection of allogenic cells that can influence the success or failure of transplantation therapy. In recent years, the usefulness of immunotherapy for treating diseases in humans by using the immune system has been demonstrated, and the importance of grasping the state of the immune system is increasing.

As a method for analyzing the state of the immune system, an analysis method based on cytokine secretion is known. In this analysis method, it is necessary to culture cells after immune stimulation of the cells of the immune system, and it takes a lot of time (tens of hours) and labor from after the immune stimulation to the detection of cytokine.

In recent years, when an immune cell and a target cell are brought into contact with each other, a structure formed on the immune cell on the contact surface has attracted attention. This structure is called an immune synapse because it is functionally and morphologically similar to the synaptic structure formed by a nerve cell. Immune synapse is suggested to be involved in the amplification of immunostimulatory signals, and it is known that the ability to form an immune synapse correlates with the ability to secrete cytokines (Carlin L M. et al., Blood, vol. 106, p. 3874-3879, 2005). It is also known that the immune synapse formation occurs in a shorter time (tens of minutes) than cytokine secretion (Carlin L M. et al., Blood, vol. 106, p. 3874-3879, 2005).

As a method for measuring an immune synapse, for example, a method of stimulating immune cells using an immunostimulator on a glass substrate, and measuring an immune synapse in T cells with a total internal reflection fluorescence microscope while maintaining the contact surface with the glass substrate is known (Yokosuka T. et al., Immunity, vol. 29, p. 589-601, 2008). Further, a method for measuring an immune synapse in T cells by imaging flow cytometry while maintaining the contact surface formed with target cells is known (Hosseini B H. et al., Proc Natl Acad Sci USA, vol. 106, p. 17852-17857, 2009). In Yokosuka T. et al., Immunity, vol. 29, p. 589-601, 2008, detection of immune synapse is performed using costimulatory molecule CD28 as an index, and in Hosseini B H. et al., Proc Natl Acad Sci USA, vol. 106, p. 17852-17857, 2009, detection of immune synapse is performed using CD3 as an index. In both Yokosuka T. et al., Immunity, vol. 29, p. 589-601, 2008 and Hosseini B H. et al., Proc Natl Acad Sci USA, vol. 106, p. 17852-17857, 2009, immune cells are observed while maintaining the contact surface with the object.

SUMMARY OF THE INVENTION

The scope of the present invention is defined solely by the appended claims, and is not affected to any degree by the statements within this summary.

It is very important to grasp the state of the immune system, that is, to quickly and easily grasp the response of cells of the immune system to various immune stimuli, in providing treatment of various immune systems.

Conventionally, in order to analyze the response of cells of the immune system to immune stimulation, an analysis method using cytokine secretion as an index has been used. However, with this analysis method, after immune stimulation, immune cells must be cultured until cytokine is secreted, which is complicated and time consuming.

When a total internal reflection fluorescence microscope was used to measure the response of cells of the immune system to various immune stimuli, the number of cells that could be measured was small, and it took time and labor to measure, so it could not be easily measured, and was not suitable for an automated device.

Therefore, there has been a demand in the art for quickly and easily grasping the response of cells of the immune system to various immune stimuli.

In order to solve the above problems, the present inventors focused on an immune synapse that was suggested to change in a shorter time as compared with cytokine secretion and be involved in amplification of immunostimulatory signals. However, since the immune synapse is a loose bond formed in the immune cell on the surface connected with the target cell (Hosseini B H. et al., Proc Natl Acad Sci USA, vol. 106, p. 17852-17857, 2009), there was a concern that dissociation occurred before measurement and during measurement. In fact, an immune synapse has not been used as an index of the response of immune cells to immune stimulation so far, in the state where the contact surface between the target cell and the immune cell was eliminated.

The present inventors have conducted extensive studies focusing on various factors known to be involved in immune synapse formation, for a method for quickly detecting the response of immune cells to immune stimulation. As a result, the present inventors have found that the ability to form an immune synapse in an immune cell can be determined even when the contact surface between the immune cell and the object has been eliminated when a surface antigen such as costimulatory molecule is used as index among various factors, thereby completing the present invention.

A first aspect of the present invention is to provide a method for measuring an immunostimulatory response of an immune cell, including (i) bringing a measurement target immune cell into contact with an immuno stimulator, (ii) forming a contact surface with a substance different from the measurement target immune cell on the measurement target immune cell, (iii) bringing the measurement target immune cell into contact with a capturing body that binds to a surface antigen on the contact surface and is capable of generating an optical signal, (iv) detecting the optical signal generated from the capturing body, and (v) determining whether or not the measurement target immune cell from which the contact surface has been eliminated before detecting the optical signal has an immunostimulatory response, based on the detected optical signal.

A second aspect of the present invention is a method for measuring an immunostimulatory response of an immune cell, including (i) bringing a measurement target immune cell into contact with an immuno stimulator, (ii) forming a contact surface with a substance different from the measurement target immune cell on the measurement target immune cell, (iii) bringing the measurement target immune cell into contact with a capturing body that binds to a costimulatory molecule on the contact surface and is capable of generating an optical signal, (iv) detecting the optical signal generated from the capturing body, and (v) automatically determining whether or not the measurement target immune cell has an immunostimulatory response, based on the detected optical signal.

A third aspect of the present invention is a method for determining ability to form an immune synapse in an immune cell, including (i) bringing a measurement target immune cell into contact with an immuno stimulator, (ii) forming a contact surface with a substance different from the measurement target immune cell on the measurement target immune cell, (iii) bringing the measurement target immune cell into contact with a capturing body that binds to a surface antigen on the contact surface and is capable of generating an optical signal, (iv) detecting the optical signal generated from the capturing body, and (v) determining localization of the surface antigen in the measurement target immune cell from which the contact surface has been eliminated before detecting the optical signal, based on the detected optical signal.

A fourth aspect of the present invention is a cell analyzer including an introduction unit for introducing a complex of an immune-stimulated measurement target immune cell and a capturing body that binds to a surface antigen of the immune cell and is capable of generating an optical signal, the capturing body being bound to a surface antigen on a contact surface between the immune cell and a substance different from the immune cell, an imaging unit for capturing an image of the complex supplied from the introduction unit, and an analyzing unit for determining whether or not the measurement target immune cell from which the contact surface has been eliminated before performing the imaging has an immunostimulatory response, based on the image captured by the imaging unit.

A fifth aspect of the present invention is a cell analyzer including an introduction unit for introducing a complex of an immune-stimulated measurement target immune cell and a capturing body that binds to a surface antigen of the immune cell and is capable of generating an optical signal, the capturing body being bound to a surface antigen on a contact surface between the immune cell and a substance different from the immune cell, a detection unit for irradiating the complex supplied from the introduction unit with light and detecting an optical signal from the complex, and an analyzing unit for determining whether or not the measurement target immune cell from which the contact surface has been eliminated before detecting the optical signal has an immunostimulatory response, based on the detected optical signal.

BRIEF DESCRIPTION OF THE DRAWINGS

FIGS. 1A, 1B and 1C represent schematic diagrams of steps (i) to (iii), respectively, according to an embodiment;

FIG. 7A is a flowchart showing control processing by the CPU 204 of the measuring device 2. FIG. 7B is a flowchart showing control processing by the CPU 301 of the information processing apparatus 3;

FIGS. 8A and 8B each depict images showing the measurement data according to Embodiment 1. FIG. 8A represents when immune stimulation was not given. FIG. 8B represents when immune stimulation was given;

FIG. 9 is a schematic diagram showing a measurement process based on the measurement data according to Embodiment 1;

FIGS. 12A to 12D show fluorescence signals detected while the cells in which costimulatory molecules CD28 are uniformly distributed on the cell membrane (FIG. 12A) and the cell in which costimulatory molecules CD28 are localized on the cell membrane (FIG. 12B) pass through the region detecting fluorescence signal (not shown) in the direction of the arrows (FIGS. 12C and 12D), respectively;

FIG. 13A is a 2D scattergram in which the pulse height (H) is assigned to the X axis and the pulse width (w) is assigned to the Y axis, and FIG. 13B is a 2D scattergram in which the pulse height (H) is assigned to the X axis and the pulse area (A) is assigned to the Y axis;

FIGS. 17A, 17B, 17C, and 17D are fluorescence images showing the distribution of CD3 and CD40L in T cells in the case without stimulation (FIGS. 17A and 17C) and in the case with stimulation (FIGS. 17B and 17D);

FIG. 20M is a 2D scattergram showing cell size (X axis) and aspect ratio (Y axis). FIG. 20B is a 2D scattergram showing the total fluorescence signal intensity of the cell (X axis) and count (Y axis);

FIGS. 21A, 21B, 21C, 21D, 21E, 21F, 21G, and 21H are superimposed images of transmitted light images and fluorescence images, showing the distribution of CD3, CD28, CD40L and OX40 in T cells in the cases without stimulation (FIGS. 21A, 21C, 21E and 21G) and in the cases with stimulation (FIGS. 21B, 21D, 21F and 21H);

DETAILED DESCRIPTION OF THE PREFERRED EMBODIMENTS

Figure 2:
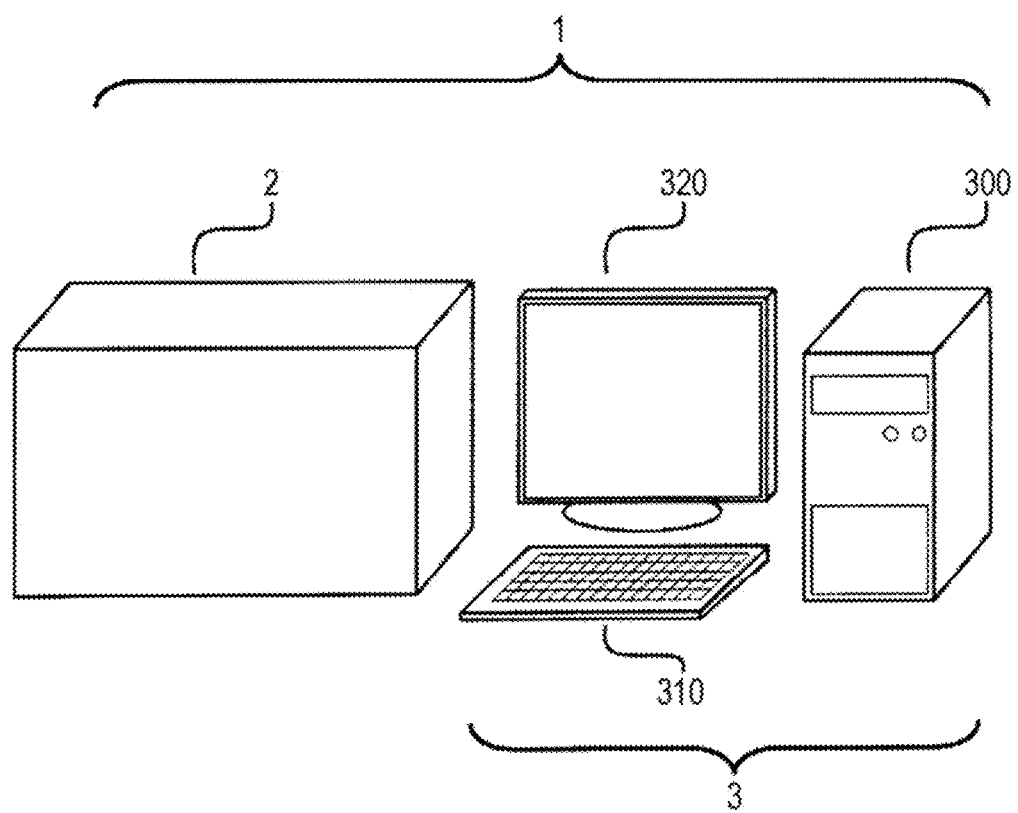
FIG. 2 is a diagram showing a configuration of the cell analyzer according to Embodiment 1.

One aspect relates to a method for measuring an immunostimulatory response of an immune cell. In this aspect, steps (i) and (ii) include forming a contact surface between a measurement target immune cell and a substance different from the measurement target immune cell, in the presence of an immunostimulator. In this embodiment, following a step (i) of bringing the measurement target immune cell into contact with the immunostimulator, a step (ii) of forming a contact surface with the substance on the measurement target immune cell may be performed. Alternatively, when the immunostimulator is present on the surface of the substance, the step (i) and the step (ii) may be performed at the same time. Even in this case, strictly speaking, the step (ii) is performed after the step (i). By performing the steps (i) and (ii), an immune synapse is formed on the contact surface of the activated immune cell.

In step (iii), in order to detect the formed immune synapse, a capturing body that binds to a surface antigen on the contact surface and is capable of generating an optical signal (hereinafter simply referred to as "capturing body") is brought into contact with the immune cell on which the contact surface is formed. It is preferable that the capturing body binds to a molecule constituting the immune synapse, among the surface antigens on the contact surface. By performing the step (iii), a complex of a molecule constituting the immune synapse and a capturing body is formed in the immune cell.

Next, in step (iv), the optical signal from the capturing body contained in the complex on the immune cell is detected. Means for detecting the optical signal is not particularly limited, but a means that can be analyzed for individual cells is preferable. Examples of such means for detecting the optical signal include a flow cytometer, an imaging cytometer, and the like. In a preferred embodiment, the step (iv) detects the optical signal generated from the capturing body bound to the surface antigen of the immune cell, using a flow cytometer or an imaging cytometer.

In step (v) described later, an immunostimulatory response is determined with respect to the immune cell from which the contact surface has been eliminated. Therefore, before the detection of the optical signal in the step (vi), an operation to eliminate the contact surface described later may be performed to the immune cell. In the case where the step (iv) is performed using a flow cytometer or an imaging cytometer, using a substance of a non-biological material described later (for example, a container, a multi-well plate, a slide or the like) as the substance different from the immune cell, the method of this embodiment preferably includes a step of eliminating the contact surface. If necessary, the immune cell may be fixed by a conventional method after elimination of the contact surface. By fixation, the localization of surface antigens can be maintained in the immune cell from which the contact surface has been eliminated. For fixation of the cells, it is preferable to use a fixing solution containing paraformaldehyde, lower alcohol and the like.

In a further embodiment, whether or not the immune cell is an immune cell from which the contact surface has been eliminated may be determined, based on the detected optical signal. Thereby, an optical signal derived from the immune cell from which the contact surface has been eliminated can be extracted, and used for determination in the step (v). For example, in the case of using an allogenic cell as a substance different from the immune cell, in the measurement with a flow cytometer, a difference occurs in the optical signal with respect to the cell size (for example, the intensity of forward scattered light or pulse width), between the immune cell from which the contact surface has been eliminated and the immune cell whose contact with the allogenic cell is maintained. In the measurement with an imaging cytometer, it is possible to distinguish between the immune cells from which the contact surface has been eliminated and the immune cells whose contact with the allogenic cell is maintained, based on the images of the imaged cells.

For illustrative purposes, reference is made to FIG. 1A which schematically shows steps (i) to (iii) according to this embodiment. FIG. 1A shows an example using an immunostimulatory antibody described later as an immunostimulator and using a plate as a substance different from an immune cell. The plate corresponds to, for example, a bottom surface of a container used for cell culture, a bottom surface of a well of a multi-well plate, a surface of a slide used for microscopic observation, or the like. In FIG. 1A, an immune cell is brought into contact with immunostimulatory antibodies in the step (i). In this example, the immunostimulatory antibody is an antibody that binds to a costimulatory molecule that is a kind of the surface antigen of the immune cell. Following the step (i), in the step (ii), the immune cell in a state in contact with the immunostimulatory antibodies is brought into contact with the plate to form a contact surface between the immune cell and the plate. In the step (iii), secondary antibodies against the immunostimulatory antibodies used in the step (i) are used to detect a costimulatory molecule in the immune cell. The secondary antibodies are labeled with a substance capable of generating an optical signal. In this example, while the contact surface has been eliminated in the step (iii), the immune cell and the capturing bodies may be brought into contact with each other in a state where the contact surface is maintained. FIG. 1A is an illustration of the steps (i) to (iii) according to one embodiment, and the present disclosure is not limited thereto.

In the step (v), whether or not the immune cell from which the contact surface has been eliminated have an immunostimulatory response is determined, based on the optical signal detected in the step (iv). In this embodiment, in the step (v), a value reflecting a distribution of surface antigens in the immune cell is measured, based on the detected optical signal, and the measured value is compared with a threshold value, whereby whether or not the immune cell has an immunostimulatory response may be determined. Here, when the capturing body contains a fluorescent substance, examples of the value reflecting the distribution of surface antigens include a pulse width, a pulse height and a pulse area of the fluorescence signal from the capturing body bound to the surface antigen, and the like.

When the capturing body contains a fluorescent substance, in the step (v), a fluorescence image may be acquired based on the fluorescence signal detected in the step (iv), and a determination may be made based on the fluorescence image. That is, in the fluorescence image, the area showing fluorescence signals that reflects the distribution of surface antigens is measured, and the measured value is compared with the threshold value, thereby determining whether or not the immune cell has an immunostimulatory response. As used herein, the term "area showing fluorescence signals" means the number of pixels showing a luminance value exceeding a predetermined threshold value in the fluorescence image. In this embodiment, while it is not limited, when the area is smaller than the threshold value, the immune cell may be determined to have the immunostimulatory response.

In a further embodiment, the step (v) may further include measuring at least one selected from the group comprising the total fluorescence signal intensity in the area, the size of the immune cell and its aspect ratio, and comparing the measured value with the threshold value. As used herein, the term "total fluorescence signal intensity" in the area or of the cell means the integrated value of the luminance value of each pixel in the area showing a luminance value exceeding the predetermined threshold value in the fluorescence image. The region of a cell membrane showing a luminance value lower than the predetermined threshold value in a transmitted light image is detected, and as used herein, the term "cell size" means the number of pixels of the image reflecting the cell surrounded by the detected cell membrane. As used herein, the cell "aspect ratio" refers to the ratio of the length to the width (the number of pixels) of the image reflecting the cell particles in the transmitted light image.

In a further embodiment, the determination on whether or not the immune cell has an immunostimulatory response based on the detected optical signal includes measuring at least one selected from the pulse width of the fluorescence signal, the pulse width of the scattered light signal, the value reflecting the fluorescence signal region per cell, and the value reflecting the cell size, and comparing the measured value with the threshold value, thereby determining whether the immune cell has the immunostimulatory response.

As used herein, the term "immune synapse" means a molecular complex that is a part responsible for immune cell activation, which is formed on the immune cell on the contact surface between the immune cell and the target cell. The molecular complex is known to be formed by gathering a receptor (for example, a T cell receptor (TCR) or NK cell receptor), a cofactor of the receptor (for example, CD3), various costimulatory molecules (for example, CD28), an adhesion molecule (for example, integrin) and a signal molecule.

As used herein, the term "contact surface" means a region where a measurement target immune cell is in contact with a substance different from the measurement target immune cell. Here, the contact between the measurement target immune cell and the substance different from the measurement target immune cell also includes an indirect contact through an interaction between molecules present on the surface of the measurement target immune cell and molecules present on the surface of the substance different from the measurement target immune cell. As described above, in the method of this embodiment, an immune synapse is formed on the contact surface. Accordingly, it can also be said that the contact surface on the immune cell is a region where an immune synapse is formed. The contact surface may be, but is not limited to, formed by a spontaneous contact of the measurement target immune cell with the substance different therefrom. Alternatively, the contact surface may be formed by bringing the measurement target immune cell into contact with the substance different from the measurement target immune cell.

As used herein, the term "measurement target immune cell" means a cell type that is responsible for a mechanism for discriminating between self and non-self and excluding non-self. The measurement target immune cell may be, but is not limited to, a T cell, a natural killer (NK) cell and a mixture thereof. The antigen-presenting cell is not included in the measurement target immune cell as referred herein, and is included in the "substance different from the measurement target immune cell" described later.

As used herein, the term "substance different from the measurement target immune cell" refers to a substance capable of providing a contact surface to the immune cell when brought into contact with the immune cell. The substance different from the measurement target immune cell may be a non-biological material or a biological material. A substance that is a non-biological material may be, but is not limited to, a container, a multi-well plate, a slide, a bead, or the like. A substance that is a biological material may be, but is not limited to, an allogenic cell, an antigen-presenting cell, a cancer cell, or the like. The allogenic cell, antigen-presenting cell and cancer cell may be an established cell line. In addition, the allogenic cell and cancer cell may be in the form of a tissue containing them. The "allogenic cell" is a non-self cell and may be a T cell, a natural killer (NK) cell and a mixture thereof.

In this embodiment, a method of bringing a measurement target immune cell into contact with a substance different from the measurement target immune cell is not particularly limited. For example, measurement target immune cells may be brought into contact by placing them in a container or a well of a multi-well plate together with a medium for precipitation. In this case, the container or the multi-well plate containing the measurement target immune cells may be centrifuged. Alternatively, the immune cells may be placed on a slide and brought into contact. In a further embodiment, when a substance different from the measurement target immune cell is in the form of particles such as beads, allogenic cells, antigen-presenting cells or cancer cells, it may be brought into contact by adding the substance to the measurement target immune cells. The contact surface can be formed by maintaining a state in which the measurement target immune cell are in contact with the substance different from the measurement target immune cell. The time for maintaining the contact state is, for example, 2 minutes or more and 60 minutes or less, preferably 10 minutes or more and 45 minutes or less, more preferably 20 minutes or more and 40 minutes or less, and particularly preferably 30 minutes.

As used herein, the term "surface antigen" is a protein, a sugar chain, a lipid and a combination thereof present on a cell membrane. The type of the surface antigen is not particularly limited as long as a capture substance capable of binding to the surface antigen is present, or such capture substance can be produced. Preferred surface antigens are molecules that constitute an immune synapse in an immune cell. Examples of such molecules include TCRα/β, CD3, CD28, CD40L (CD40 ligand), OX40, CTLA4 (cytolytic T lymphocyte associated antigen-4), PD-1 (programmed cell death-1) and ICOS (inducible costimulatory molecule), and the like. The costimulatory molecule described later is also a kind of surface antigen of the immune cell.

In this embodiment, the measurement target immune cell is at least one selected from a T cell and an NK cell. In a further embodiment, the measurement target immune cell is a T cell or an NK cell. In a preferred embodiment, the measurement target immune cell is a T cell.

The T cell may be, but is not limited to, an effector T cell such as a helper T cell (also referred to as "$CD4^+$ T cell"), a suppressor T cell, a regulatory T cell, a cytotoxic T lymphocyte (CTL, also referred to as "$CD8^+$ T cell"), a naive T cell, and a genetically modified cell. The effector T cell may be, but is not limited to, a cell activated in vivo and in vitro. These T cells may be used singly or as a T cell subpopulation containing two or more kinds.

In this embodiment, the measurement target immune cell may be prepared from a biological sample. For example, the immune cell may be isolated from blood (for example, peripheral blood and umbilical cord blood) or bone marrow fluid, by a known cell separation method. Examples of such cell separation method include a method of fractionating a desired cell from a biological sample containing cells, based on cell size, aggregation degree and/or specific gravity. For example, the cells can be fractionated based on cell size or aggregation degree, using a commercially available cell sorter. In addition, the cells can be fractionated based on the specific gravity of cells, by specific gravity gradient centrifugation. In this embodiment, the cells isolated from the biological sample may be cultured and proliferated according to a conventional method. In a further embodiment, the immune cells may be used in the form of a biological sample, such as blood (for example, peripheral blood and umbilical cord blood) or bone marrow fluid. The biological sample may be, but is not limited to, a sample obtained from mammals, for example, human and non-human mammals (for example, companion animals such as dogs and cats, domestic animals such as horses and cows).

In a further embodiment, the measurement target immune cells may be present in a sample. Thus, this embodiment provides a method for performing the method of the present disclosure on a sample containing the measurement target immune cells. More specifically, this embodiment provides a method for measuring an immunological response of a sample containing an immune cell, including (i) bringing an immune cell in the sample into contact with an immunostimulator, (ii) forming a contact surface with a substance different from the immune cell on the immune cell in the sample, (iii) bringing the immune cell in the sample into contact with a capturing body that binds to a surface antigen on the contact surface and is capable of generating an optical signal, (iv) detecting the optical signal generated from the capturing body, and (v) determining whether or not the immune cell from which the contact surface in the sample has been eliminated has an immunostimulatory response, based on the detected optical signal. The sample containing the immune cell may be the biological sample described above.

In this embodiment, in the step (v), a value reflecting a distribution of surface antigens to which the capturing body is bound in the immune cell is measured, based on the optical signal detected in the step (iv), and the measured value is compared with a threshold value, whereby whether or not the immune cell has an immunostimulatory response may be determined. When the capturing body contains a fluorescent substance, in the step (v), a fluorescence image may be acquired based on the fluorescence signal detected in the step (iv), and a determination may be made based on the fluorescence image. In the fluorescence image, the area showing fluorescence signals that reflects the distribution of surface antigens is measured, and based on the area, for example, the proportion of cells having an immunostimulatory response in the sample may be calculated. Then, the determination may be made by comparing the proportion with the proportion of immune cells having an immunostimulatory response standardized for a sample derived from a healthy subject. For example, when the proportion of the sample is higher than the standardized proportion, the sample may be determined to have a high immunological response or have an immunological response.

In the present specification, the "immune stimulation" on the immune cell includes bringing the immune cell into contact with an immunostimulator and forming a contact surface with a substance different from the immune cell. In this embodiment, the immune stimulation may be performed by bringing the immune cell into contact solely with the immunostimulator. In a further embodiment, the immune stimulation may be performed by bringing the immune cell into contact with the immunostimulator present on the substance. In this case, the immune cell comes into contact with the immunostimulator, as well as comes into contact with the substance.

As used herein, the term "immunostimulator" means a substance capable of acting on the immune cell to induce activation of the immune cell. Activation of the immune cell means, for example, proliferation of the immune cell, its enhanced motility or cytokine secretion. The immunostimulator may be, but is not limited to, immunostimulatory antibodies, immunostimulatory peptides, major histocompatibility molecules (MHC molecules), as well as various immunostimulators present on allogenic cells, antigen-presenting cells, and cancer cells. The immunostimulators may be used singly or in combination of two or more, or may be used in the form of an immunostimulator alone or in a complex with other substance or a substance. The immunostimulator may be, for example, in the form of a complex of an MHC molecule and an antigenic peptide, in the form fixed on a non-biological material such as a bead or a container, or in the form presented on an antigen-presenting cell.

In this embodiment, the immunostimulator is at least one selected from immunostimulatory antibodies, immunostimulatory peptides, MHC molecules, and complexes of an MHC molecule and an antigenic peptide. In a further embodiment, the immunostimulator may be an immunostimulatory antibody, an immunostimulatory peptide, an MHC molecule, or a complex of an MHC molecule and an antigenic peptide. In a specific embodiment, the immunostimulator is an immunostimulatory antibody.

As used herein, the term "immunostimulatory antibody" means an antibody capable of specifically stimulating an immune cell to induce activation of the immune cell. The immunostimulatory antibody may be, but is not limited to, an anti-TCR α/β antibody, an anti-CD3 antibody, an anti-CD40L antibody, an anti-OX40 antibody, an anti-CD2 antibody, an anti-CD28 antibody, an anti-CD137 antibody, an anti-CTLA4 antibody, an anti-PD-1 antibody, an anti-ICOS antibody, and an anti-integrin antibody (an anti-CD2 antibody). These immunostimulatory antibodies may be used singly or in combination of two or more. The immunostimulatory antibodies may be used an antibody alone or in a state immobilized on other substance, for example, a non-biological material such as a bead, a multi-well plate, a slide or a container.

In one embodiment, the immunostimulatory antibody is at least one selected from anti-TCR α/β antibodies, anti-CD3 antibodies, anti-CD40L antibodies, anti-OX40 antibodies, anti-CD2 antibodies, anti-CD28 antibodies, anti-CD137 antibodies, anti-CTLA4 antibodies, anti-PD-1 antibodies, anti-ICOS antibodies and anti-integrin antibodies (anti-CD2 antibodies). In a further embodiment, the immunostimulatory antibody is at least one selected from anti-CD3 antibodies and anti-CD28 antibodies. In a specific embodiment, the immunostimulatory antibody is an anti-CD3 antibody or an anti-CD28 antibody.

The antibody may be either a monoclonal antibody or a polyclonal antibody unless otherwise specified. In addition, the antibody may be an antibody fragment, a single chain antibody or a derivative thereof.

As used herein, the term "immunostimulatory peptide" means a peptide capable of stimulating an immune cell to induce activation of the immune cell. The immunostimulatory peptide is, for example, an antigenic peptide (such as an antigenic peptide of *Mycobacterium tuberculosis*).

In this embodiment, the immunostimulatory peptide is an antigenic peptide. The antigenic peptides may be used singly or in combination of two or more. In a specific embodiment, the antigenic peptide may be used in the form of a complex with an MHC molecule presented on the MHC molecule.

As used herein, the term "major histocompatibility molecule (MHC molecule)" means a molecule that is responsible for alloantigenicity that causes the strongest rejection in allotransplantation of organs, tissues and cells. An HLA molecule in human and an H-2 molecule in mouse correspond to the MHC molecule. The MHC molecules include class I molecules and class II molecules. The MHC class I molecule is expressed on almost all nucleated cells, forms a complex with the peptide produced in the cell and presents it to the receptor of CTL (CD8-positive T cell). The MHC class II molecule is expressed only on so-called antigen-presenting cells such as macrophages and B cells, and presents peptides derived from foreign antigens to the receptor of helper T cell (CD4-positive T cell).

In this embodiment, when the immunostimulator is an MHC molecule or a complex of an MHC molecule and an antigenic peptide, the MHC molecule may be either an MHC class I molecule or an MHC class II molecule. The MHC molecule or the complex of an MHC molecule and an antigenic peptide may be used in the form present on a cell membrane of an antigen-presenting cell, a cancer cell or the like.

As used herein, the phrase "capturing body that binds to a surface antigen and is capable of generating an optical signal" includes a substance that binds to a surface antigen of the immune cell and a substance capable of generating an optical signal. Examples of the substance that binds to a surface antigen include, but are not limited to, antibodies, antibody fragments, single chain antibodies, aptamers and the like that bind to a surface antigen of the immune cell. In this embodiment, the capturing body contains a substance capable of generating an optical signal, and an antibody, an antibody fragment, a single chain antibody or an aptamer that binds to a surface antigen.

The substance that binds to a surface antigen may directly bind to a surface antigen or indirectly bind to a surface antigen. As used herein, the phrase "indirectly binds to a surface antigen" means binding to a surface antigen via one or a plurality of molecules. The substance that indirectly binds to a surface antigen binds to, but is not limited to, other substance bound to a surface antigen. That is, the substance that indirectly binds to a surface antigen indirectly binds to the surface antigen via the other substance.

Examples of the substance capable of generating an optical signal include, but are not limited to, fluorescent substances. As the fluorescent substance, a known fluorescent dye, a fluorescent protein or the like can be used without particular limitation. The substance capable of generating an optical signal may be, but is not limited to, chemically bound to the capturing body that binds to a surface antigen. Examples of such capturing body include fluorescently labeled antibodies that directly bind to the surface antigen (see capturing bodies in FIGS. 1B and 1C).

In this embodiment, the capturing body that binds to the surface antigen and is capable of generating an optical signal includes a substance that directly binds to the surface antigen and a substance capable of generating an optical signal. In this embodiment, the capturing body may be, but is not limited to, an antibody, an antibody fragment, a single chain antibody or an aptamer that directly binds to a surface antigen, to which a substance capable of generating an optical signal is bound.

Alternatively, the capturing body may include a substance that indirectly binds to a surface antigen and a substance capable of generating an optical signal. In this embodiment, the capturing body is an antibody, an antibody fragment, a single chain antibody or an aptamer that binds to other substance bound to a surface antigen, to which a substance capable of generating an optical signal is bound. For example, but not by way of limitation, an antibody that specifically binds to a surface antigen is bound to the surface antigen as a primary antibody, and then an antibody that specifically binds to the primary antibody is bound thereto as a secondary antibody. The substance capable of generating an optical signal is bound to the secondary antibody. In this example, the secondary antibody becomes a capturing body that binds to a surface antigen and is capable of generating an optical signal (see the capturing body in FIG. 1A). Also, the primary antibody may be an immunostimulatory antibody.

The surface antigen to which the capturing body binds may be a costimulatory molecule of the immune cell. As used herein, the term "costimulatory molecule" means a substance present in a T cell that can provide the T cell with an antigen-specific signal via a T cell receptor (TCR) upon immune cell activation, as well as an auxiliary signal for activating the T cell. As used herein, when the "costimulatory molecule" is present in an NK cell, it comprises a substance that can provide the NK cell with a ligand-specific signal of the target cell via an activating receptor of NK cell, as well as an auxiliary signal for activating NK cell. The costimulatory molecule may be, but is not limited to, CD28, OX40, CD40L, CTLA4, PD-1 or ICOS.

In this embodiment, the substance different from the immune cell is at least one selected from biological materials, for example, allogenic cells, antigen-presenting cells, and cancer cells. In a further embodiment, the substance different from the immune cell is an allogenic cell, an antigen-presenting cell, or a cancer cell. In a specific embodiment, the substance different from the immune cell is an allogenic cell. In a specific embodiment, the substance different from the immune cell is an antigen-presenting cell. In a specific embodiment, the substance different from the immune cell is a cancer cell.

When a cell except immune cell such as an allogenic cell, an antigen-presenting cell and a cancer cell is used as the substance different from the immune cell, the immunostimulator in the step (i) is various immunostimulators such as MHC molecules and the like present on the cell. For example, when the substance different from the immune cell is an allogenic cell, the immunostimulator includes, but is not limited to, at least an MHC molecule. When the substance different from the immune cell is an antigen-presenting cell, the immunostimulator includes, but is not limited to, at least a complex of an MHC class II molecule and an antigenic peptide. When the substance different from the immune cell is a cancer cell, the immunostimulator includes, but is not limited to, at least a complex of an MHC class I molecule and a cancer antigenic peptide.

The step (i) includes bringing an immune cell into contact with at least one type of a substance different from the immune cell selected from an allogenic cell, an antigen-presenting cell, and a cancer cell, thereby bringing the immune cell into contact with the immunostimulator on the substance. The step (ii) includes maintaining the contact state between the immune cell and the substance contacted in the step (i), thereby forming a contact surface with the substance on the immune cell.

In this embodiment, the substance different from the immune cell is preferably a non-biological material, for example, an instrument usually used in the field of life science. Such instrument includes containers, multi-well plates, slides, or beads, and the like. Examples of the container include dishes, bottles, tubes and the like. According to this embodiment, since the substance is a non-biological material, it has industrial advantages such as easiness of handling and capable of being stored for a long period, as compared with the case of using a biological material as the substance. In a specific embodiment, the container, multi-well plate, slide or bead that is the substance contains an immunostimulator on its surface. For example, when the immunostimulator is an immunostimulatory antibody, the antibody may be immobilized on the surface of a container, multi-well plate, slide or bead. Alternatively, the container, multi-well plate, slide or bead that is the substance does not contain an immunostimulator on its surface.

In this embodiment, after bringing the immunostimulator with the immune cell in the step (i), the substance different from the immune cell in the step (ii) may contain a further immunostimulator on its surface. In this embodiment, for the purpose of additional immune stimulation, a substance having an immunostimulator of the same or different kind as the immunostimulator in the step (i) on its surface may be used in the step (ii). For example, in the step (i), an antibody against a costimulatory molecule is used as an immunostimulator, and in the step (ii), a multi-well plate in which an anti-CD3 antibody is immobilized on the surface of the well can be used as a substance different from the immune cell. Alternatively, the substance in the step (ii) may not contain a further immunostimulator on its surface.

In this embodiment, when an immunostimulatory antibody is used as the immunostimulator in the step (i), this immunostimulator may be used in common as the capturing body in the step (iii). In this embodiment, the immunostimulator may be, for example, a complex of an anti-CD28 antibody, an anti-CD3 antibody, an anti-CD40L antibody, an anti-OX40 antibody, an anti-CTLA4 antibody, an anti-PD-1 antibody, an anti-ICOS antibody, an antibody fragment thereof, a single chain antibody, and a combination of one or more thereof, which is labeled with a substance capable of generating an optical signal. By using such labeled immunostimulatory antibody, immune stimulation to the immune cell in the step (i) and capture of the surface antigen of the immune cell in the step (iii) can be performed at the same time.

Accordingly, a further embodiment is a method for measuring an immunostimulatory response of an immune cell, including (i) bringing an immune cell into contact with an immunostimulator, (ii) forming a contact surface with a substance different from the measurement target immune cell on the immune cell, (iv) detecting the optical signal generated from the capturing body, and (v) determining whether or not the immune cell has an immunostimulatory response, based on the detected optical signal, the immunostimulator being an immunostimulatory antibody labeled with a substance capable of generating an optical signal. According to this embodiment, the number of reagents and the number of steps can be reduced because the immunostimulator also serves as a capturing body that binds to the surface antigen in the immune cell and is capable of generating the optical signal. Therefore, this embodiment has advantages in cost and labor.

In this embodiment, the immunostimulator in the step (i) may be present on the substance different from the immune cell in the step (ii). In this embodiment, the immunostimulator is preferably a molecule such as an immunostimulatory antibody, an immunostimulatory peptide or an MHC molecule, or a complex of an MHC molecule and an antigenic peptide. The immunostimulator may be, but is not limited to, immobilized on a container, a multi-well plate, a slide or a bead. For example, when the immunostimulator is an immunostimulatory antibody or an immunostimulatory peptide, the mode of immobilization is not particularly limited, and, for example, may be physical adsorption. Alternatively, when the immunostimulator is modified with biotin, and avidin (or streptavidin) is fixed to the surface of the substance different from the immune cell, the immunostimulator can be immobilized to the substance via bonding between biotin and avidin (or streptavidin). Also, when the immunostimulator is an MHC molecule of an allogenic cell, antigen-presenting cell, cancer cell or the like, or a complex of an MHC molecule and an antigenic peptide, the cell may be adhered to or deposited on a container, a multi-well plate, a slide or a bead. In this embodiment, the immunostimulator on the substance can be brought into contact with an immune cell to induce activation of the immune cell. According to this embodiment, the step (i) includes bringing an immune cell into contact with the substance on which the immunostimulator is immobilized on the surface, thereby bringing the immune cell into contact with the immunostimulator on the substance. The step (ii) can form a contact surface with the substance on the immune cell by maintaining the contact state between the immune cell and the substance contacted in the step (i).

Accordingly, a further embodiment provides a method for measuring an immunostimulatory response of an immune cell, including (i) bringing an immune cell into contact with an immunostimulator on a substance different from the immune cell on the immune cell, (ii) forming a contact surface with the substance on the immune cell, (iii) bringing the immune cell into contact with a capturing body that binds to a surface antigen and is capable of generating an optical signal, (iv) detecting the optical signal generated from the capturing body, and (v) determining whether or not the immune cell from which the contact surface has been eliminated has an immune response, based on the detected optical signal. According to this embodiment, the step (i) and the step (ii) can be performed substantially simultaneously by merely bringing an immune cell into contact with a substance on which the immunostimulator is immobilized on the surface. Therefore, this embodiment has an advantage that the number of steps can be reduced.

FIG. 1B is a diagram schematically showing the steps (i) to (iii) of the above embodiment. In FIG. 1B, the immunostimulator is an immunostimulatory antibody, and the substance different from the immune cell is a plate, and it is shown that the immunostimulatory antibodies are immobilized on the plate. As shown in FIG. 1B, an immune cell is brought into contact with a plate immobilized with immunostimulatory antibodies, whereby immune stimulation by the antibodies (step (i)) and contact surface formation (step (ii)) can be performed substantially simultaneously. Then, in the step (iii), capturing bodies that directly bind to surface antigens and are capable of generating an optical signal are bound to immune synapses on the immune cell. In this example, while the contact surface has been eliminated in the step (iii), the immune cell and the capturing bodies may be brought into contact with each other in a state where the contact surface is maintained. FIG. 1B is an illustration of the steps (i) to (iii) according to one embodiment, and the present disclosure is not limited thereto.

In a further embodiment, the immunostimulator may be, but is not limited to, immobilized on beads. For example, stimulation of immune cells and isolation of immune cells can be performed simultaneously by using beads immobilized with immunostimulatory antibodies. In the case where immune cells are contained in a biological sample, when the above beads are added to the sample, the immune cells in the sample are captured by the beads by immunostimulatory antibodies. Then, the biological sample containing the beads is centrifuged, whereby immune cells can be separated from the sample. When the beads are magnetic beads, biological samples containing beads may be magnetically separated. At this time, the separated immune cells are immunostimulated by an immunostimulatory antibody on the beads. In this embodiment, the contact surface between the immune cells and the beads may be eliminated before and during measurement.

FIG. 1C is a diagram schematically showing the steps (i) to (iii) of the above embodiment. In FIG. 1C, the immunostimulator is an immunostimulatory antibody, and the substance different from the immune cell is a bead, and it is shown that the immunostimulatory antibodies are immobilized on the bead. As shown in FIG. 1C, an immune cell is brought into contact with beads immobilized with immunostimulatory antibodies, whereby immune stimulation by the antibodies (step (i)) and contact surface formation (step (ii)) can be performed substantially simultaneously. Then, in the step (iii), capturing bodies that directly bind to surface antigens and are capable of generating an optical signal are bound to immune synapses on the immune cell. In this example, while the contact surface has not been eliminated in the step (iii), but the immune cell from which the contact surface has been eliminated may be brought into contact with the capturing bodies. FIG. 1C is an illustration of the steps (i) to (iii) according to one embodiment, and the present disclosure is not limited thereto.

As used herein, the term "immune cell from which the contact surface has been eliminated" means immune cell in which the contact region formed between the immune cell and the substance different from the immune cell has disappeared. That is, it means that the immune cell is separated from the substance different from the immune cell. The method for eliminating the contact surface may be, but is not limited to, a physical treatment such as pipetting, tapping, stirring, shaking or ultrasonication to a container containing the immune cells and a culture solution and the like, a chemical treatment using a chemical such as a surfactant, and a biochemical treatment using a biochemical product such as an enzyme.

In a preferred embodiment, the contact surface is eliminated by a physical treatment such as pipetting, tapping, stirring, shaking or ultrasonication. In a specific embodiment, the method is pipetting. In this embodiment, when the contact surface is eliminated, in the step (iv), the optical signal generated from the capturing body may be detected using a flow cytometer.

As used herein, the term "flow cytometer" means a measuring device for measuring the size of individual cells in the cell population and distribution of the expression level of membrane proteins, by irradiating cells in a water stream with excitation light and measuring fluorescence or scattered light emitted from the individual cells. In general, the flow cytometer has the advantages of objectively measuring a large number of cells (tens of thousands of cells/sec at maximum) in a short time, quantitatively measuring with high sensitivity, acquiring multiple parameters at the same time, and the like, as compared with general fluorescence microscope observation. As used herein, a flow cytometer has a flow channel system allowing measurement of cells in a state where cells are aligned in a liquid so that the cells can be individually measured. Such flow channel system may be realized by a part based on fluid dynamics called a flow cell. In general, the flow cell is realized by hydrodynamic focusing utilizing a sheath flow of a sheath liquid so as to enclose a sample flow, but is not limited thereto. For example, the flow cell may be realized by microcapillary or acoustic focusing.

In the present disclosure, a commercially available flow cytometer can be used without particular limitation. As used herein, the flow cytometer includes a so-called "imaging flow cytometer" that includes an imaging unit using a camera and is capable of acquiring images of cells flowing in the liquid. As described later in Embodiment 1, according to the imaging flow cytometer, multiple parameters including cell size and aspect ratio can be obtained based on the image of the imaged cell. As used herein, the flow cytometer includes both an imaging flow cytometer and a non-imaging flow cytometer. In a preferred embodiment, the flow cytometer is an imaging flow cytometer. In the present disclosure, a commercially available flow cytometer can be used without particular limitation.

In this embodiment, in the step (iv), when the substance different from the immune cell is at least one selected from an allogenic cell, an antigen-presenting cell and a cancer cell, or in the case of a bead, a complex of the immune cell, the substance different from the immune cell and the capturing body may be measured with a flow cytometer or an imaging cytometer to acquire the optical signal generated from the capturing body in the complex. Alternatively, when the substance different from the immune cell is a container, a multi-well plate or a slide, the contact surface between the immune cell and the substance different from the immune cell is eliminated, and a complex of the immune cell and the capturing body may be measured with a flow cytometer or an imaging cytometer to acquire the optical signal generated from the capturing body in the complex.

As used herein, the term "imaging cytometer" means a statistically highly accurate cell measuring device that can acquire fluorescence images, scattered light, and transmitted light images of a large number (several thousands to several millions) of individual cells in a short time (several seconds to several minutes) and quantitatively measure them. It is a measuring device that can extract information for each cell, by cell image processing. In the present disclosure, a commercially available imaging cytometer can be used without particular limitation.

In a further embodiment, a method for evaluating the activation state of the immune system in a subject is provided. This embodiment includes performing the above-described present disclosure on a biological sample containing immune cells obtained from the subject. More specifically, the evaluation method of this embodiment includes (i) bringing an immune cell in a biological sample into contact with an immunostimulator, (ii) forming a contact surface with a substance different from the immune cell on the immune cell in the biological sample, (iii) bringing the immune cell in the biological sample into contact with a capturing body that binds to a surface antigen in the immune cell and is capable of generating an optical signal, (iv) detecting the optical signal generated from the capturing body, and (v) determining whether or not the sample has an immunostimulatory response, based on the detected optical signal.

In the evaluation method of this embodiment, the capturing body contains a fluorescent substance, and in the step (v), a fluorescence image may be acquired based on the fluorescence signal detected in the step (iv), and a determination may be made based on the fluorescence image. In the fluorescence image, the area showing fluorescence signals that reflects the distribution of surface antigens is measured, and based on the area, for example, the proportion of immune cells having an immunostimulatory response in the biological sample may be calculated. Then, the determination may be made by comparing the proportion with the proportion of immune cells having an immunostimulatory response standardized for a biological sample derived from a healthy subject. In this embodiment, for example, when the proportion of the sample is higher than the standardized proportion, the sample may be determined to have a high immunological response or have an immunological response. Alternatively, in this evaluation method, the proportion of immune cells having an immunostimulatory response in a biological sample containing immune cells obtained from a subject may be compared with the proportion for a previous biological sample derived from the same subject. For example, when the proportion of the sample is higher than the previous proportion, the subject may be determined to have an improved immunological response or have an immunological response.

Other aspect relates to a method for measuring an immunostimulatory response of an immune cell, using a capturing body that binds to a costimulatory molecule in the immune cell and is capable of generating an optical signal.

In the method of this aspect, it is the same as that described in the method of the above-described embodiment, except for using the capturing body that binds to a costimulatory molecule in the immune cell and is capable of generating an optical signal, as the capturing body. Examples of the costimulatory molecule to which the capturing body binds include CD28, OX40, CD40L, CTLA4, PD-1 and ICOS.

Other aspect relates to a cell analyzer for analyzing the activation state of immune cells. Embodiments according to this aspect will be described with reference to the accompanying drawings. The following descriptions are all illustrative and not restrictive, and do not limit the invention defined in the appended claims in any way.

Embodiment 1 of Cell Analyzer

Referring to FIG. 2, a cell analyzer 1 includes a measuring device 2 and an information processing apparatus 3. The measuring device 2 optically measures a sample containing a complex of a capturing body that binds to a surface antigen of an immune cell and is capable of generating an optical signal, and the immune cell, by a flow cytometer. The information processing apparatus 3 analyzes the measurement result by the measuring device 2 and displays the analysis result on a display unit 320.

Figure 3:
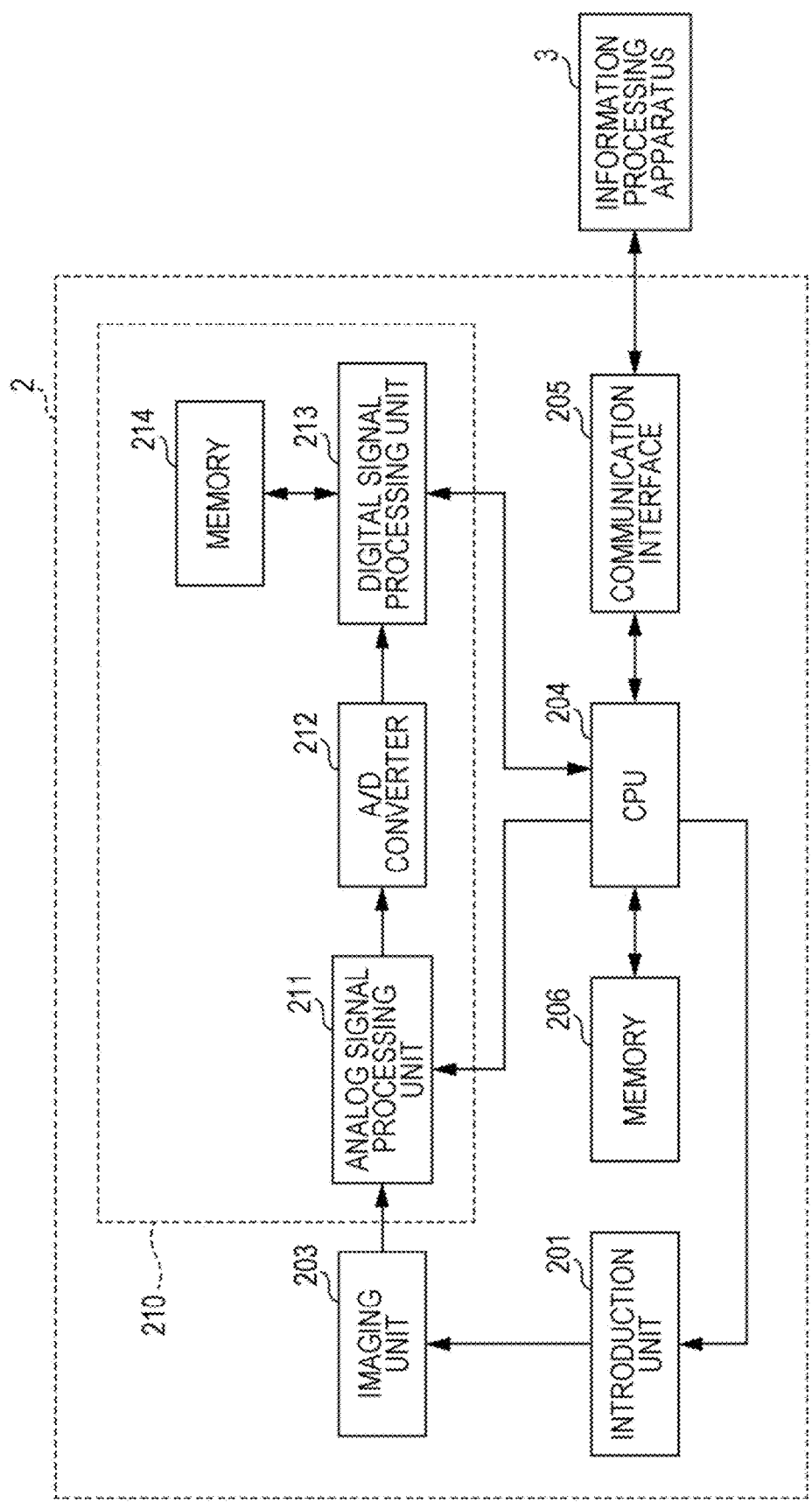
FIG. 3 is a diagram showing a configuration of the measuring device according to Embodiment 1.

Referring to FIG. 3, the measuring device 2 has an introduction unit 201, an imaging unit 203, a signal processing unit 210, a CPU 204, a communication interface 205, and a memory 206. The signal processing unit 210 has an analog signal processing unit 211, an A/D converter 212, a digital signal processing unit 213, and a memory 214.

In this embodiment, the introduction unit 201 includes a container and a pump (not shown). The sample in the container is supplied to a flow cell 203c (see FIG. 4) of the imaging unit 203 together with a sheath liquid by a pump. The introduction unit 201 supplies the sample to the imaging unit 203 in accordance with the instructions from the CPU 204. In Embodiment 1, a complex obtained by giving immune stimulation including a contact with an anti-CD28 antibody to clonal T cells derived from human peripheral blood, then immobilizing the cells, and secondarily staining the cells using a phycoerythrin (PE)-labeled anti-mouse IgG antibody bound to the anti-CD28 antibody is used as a measurement sample.

The imaging unit 203 irradiates the sample supplied from the introduction unit 201 with a laser beam, images the complex, and outputs image information of the generated transmitted light image and fluorescence image as an electric signal to the analog signal processing unit 211. The analog signal processing unit 211 amplifies the electric signal outputted from the imaging unit 203 in accordance with the instructions from the CPU 204, and outputs it to the A/D converter 212.

The A/D converter 212 converts the electric signal amplified by the analog signal processing unit 211 into a digital signal and outputs it to the digital signal processing unit 213. In accordance with the instructions from the CPU 204, the digital signal processing unit 213 performs predetermined signal processing on the digital signal outputted from the A/D converter 212, and measurement data is generated. The generated measurement data is stored in the memory 214.

The measurement data stored in the memory 214 includes transmitted light images and fluorescence images based on transmitted light and fluorescence generated when the complex passed through the flow cell 203c.

The CPU 204 outputs the measurement data stored in the memory 214 to the communication interface 205. The CPU 204 receives a control signal from the information processing apparatus 3 via the communication interface 205 and controls each unit of the measuring device 2 according to the control signal.

The communication interface 205 transmits the measurement data outputted from the CPU 204 to the information processing apparatus 3, and receives the control signal outputted from the information processing apparatus 3. The memory 206 is used as a work area of the CPU 204.

Figure 4:
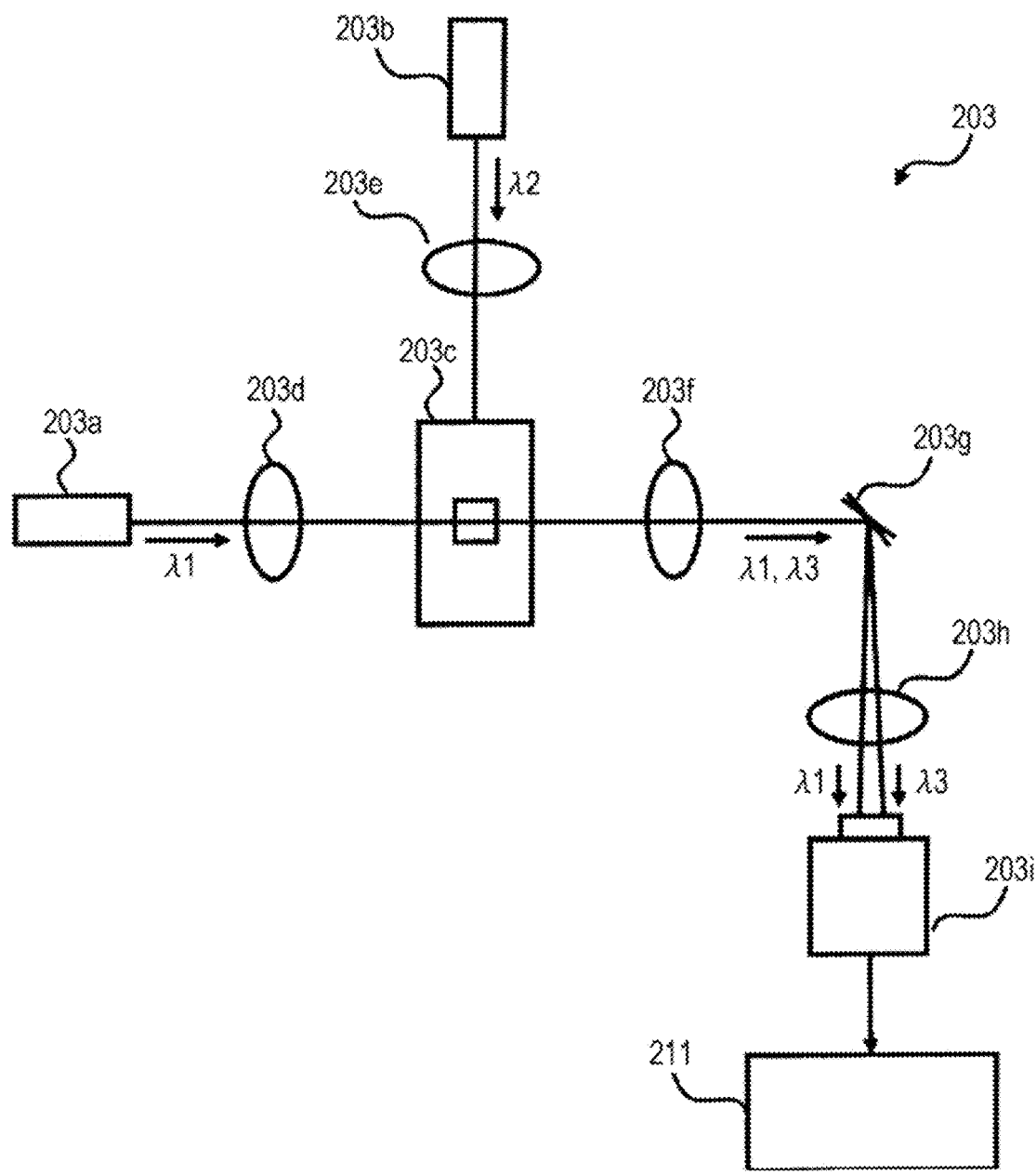
FIG. 4 is a diagram showing a configuration of the imaging unit according to Embodiment 1.

Referring to FIG. 4, the imaging unit 203 includes light sources 203a and 203b, a flow cell 203c, condenser lenses 203d and 203e, an objective lens 203f, an optical unit 203g, a condenser lens 203h, and a camera 203i.

In this embodiment, the light source 203a is a semiconductor laser light source. The light irradiated from the light source 203a is a laser beam of wavelength $\lambda 1$. The condenser lens 203d collects the light irradiated from the light source 203a and guides it to the sample in the flow cell 203c. The light of wavelength $\lambda 1$ irradiated from the light source 203a is irradiated onto the sample passing through the inside of the flow cell 203c, whereby transmitted light of wavelength $\lambda 1$ is generated from the immune cell.

The light source 203b is a semiconductor laser light source. The light irradiated from the light source 203b is a laser beam of wavelength $\lambda 2$. In this embodiment, wavelength $\lambda 2$ is about 488 nm. The condenser lens 203e collects the light irradiated from the light source 203b and guides it to the sample in the flow cell 203c. The light of wavelength $\lambda 2$ irradiated from the light source 203b is irradiated onto the sample passing through the inside of the flow cell 203c, whereby fluorescence of wavelength $\lambda 3$ is generated from PE.

The objective lens 203f collects the transmitted light of wavelength $\lambda 1$ and the fluorescence of wavelength $\lambda 3$. The optical unit 203g has a configuration in which two dichroic mirrors are combined. The two dichroic mirrors of the optical unit 203g reflect the transmitted light of wavelength $\lambda 1$ and the fluorescence of wavelength $\lambda 3$ at mutually different angles and are separated on the light receiving surface 203ia (see FIG. 5) of the camera 203i described later. The condenser lens 203h collects the transmitted light of wavelength $\lambda 1$ and the fluorescence of wavelength $\lambda 3$. The camera 203i receives the transmitted light of wavelength $\lambda 1$ and the fluorescence of wavelength $\lambda 3$ and outputs image information of the sample in the flow cell 203c as an electric signal to the analog signal processing unit 211. The camera 203i may be a TDI (Time Delay Integration) camera. With a TDI camera, image information with higher accuracy can be acquired.

Figure 5:
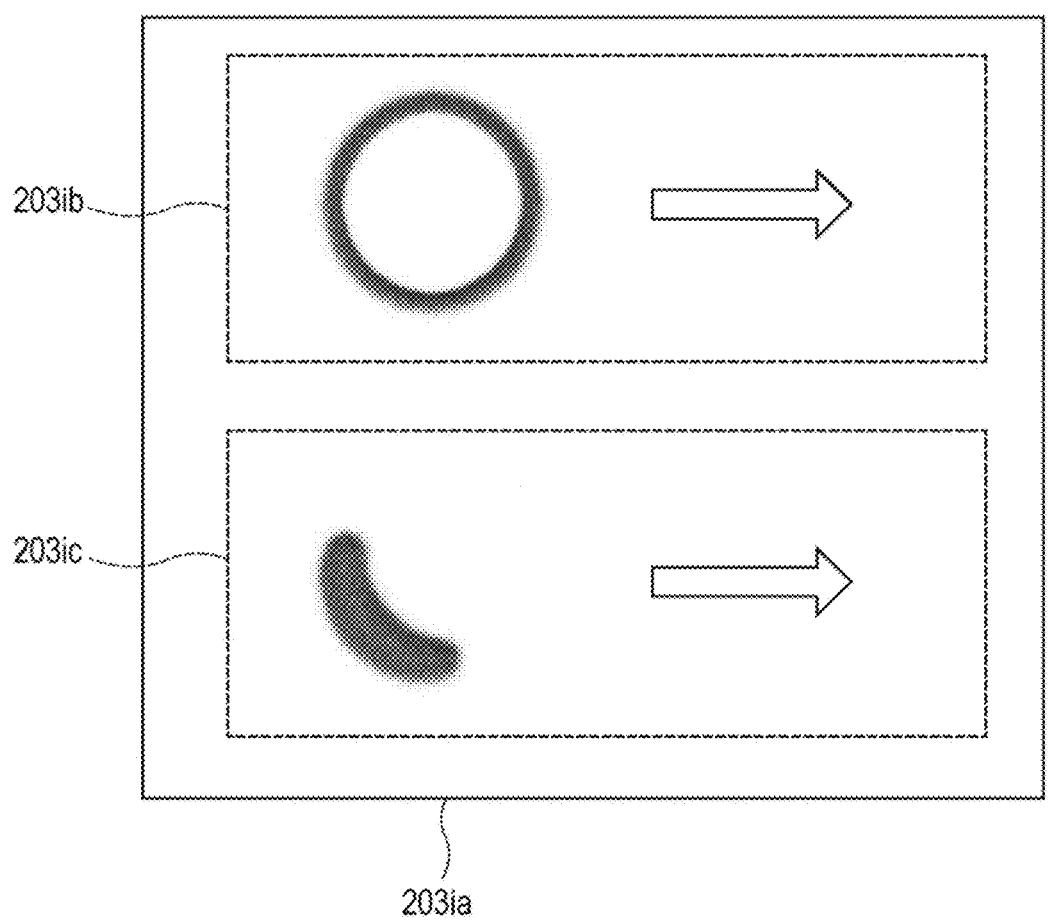
FIG. 5 is a schematic diagram showing a region on the light receiving surface of the camera according to Embodiment 1.

As shown in FIG. 5, the camera 203i receives the transmitted light of wavelength $\lambda 1$ and the fluorescence of wavelength $\lambda 3$ in the light receiving regions 203ib and 203ic on the light receiving surface 203ia, respectively. The light receiving surface 203ia is a light receiving surface of an image pickup element such as a CMOS image sensor disposed in the camera 203i. The positions of the lights irradiated on the light receiving surface 203ia move within the light receiving regions 203ib and 203ic, respectively, as the sample moves in accordance with the movement of the flow cell 203c, as indicated by the arrows. As described above, since the two lights are separated on the light receiving surface 203ia by the optical unit 203g, the CPU 204 can extract signals corresponding to each light from the image signal outputted by the camera 203i.

Figure 6:
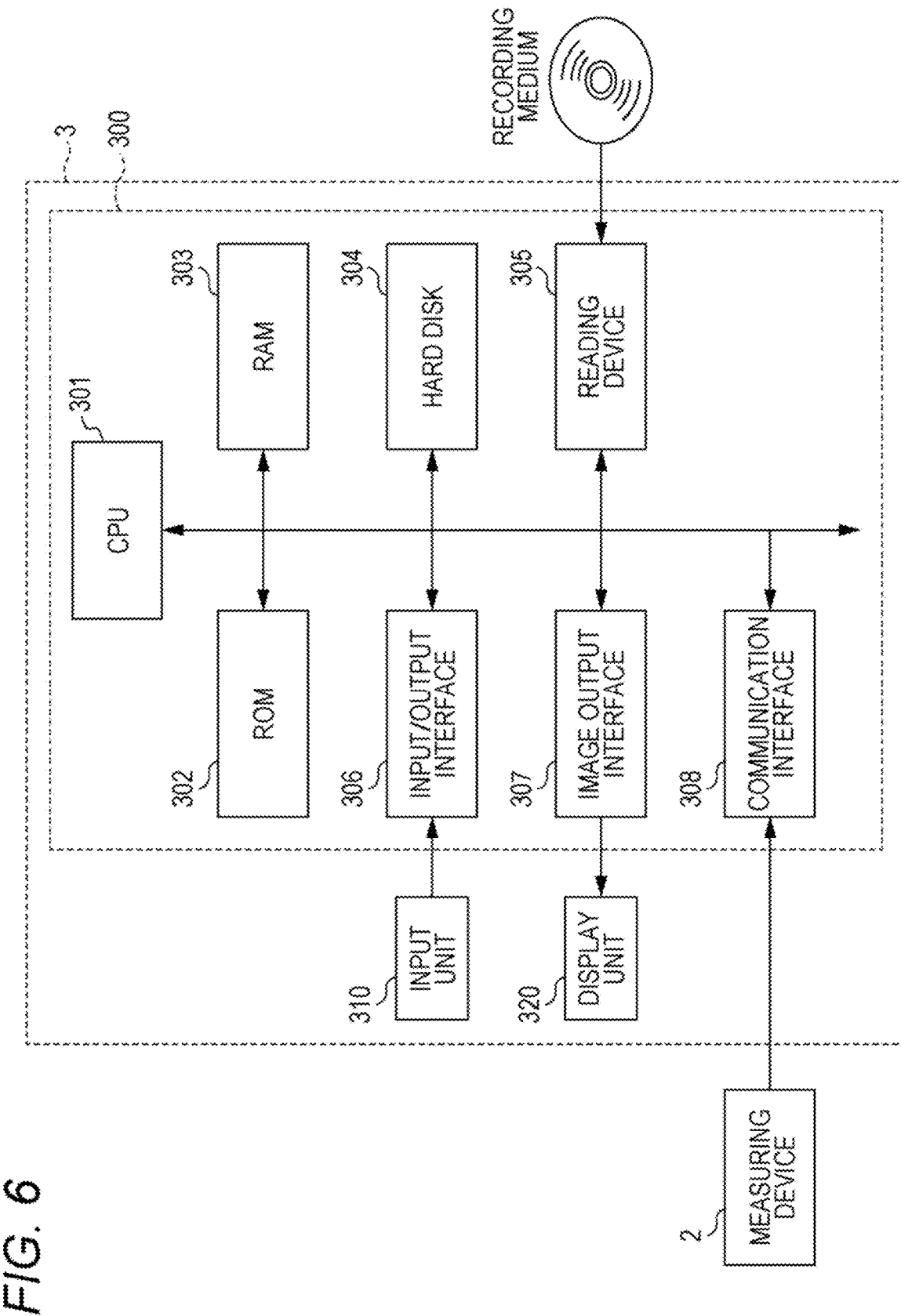
FIG. 6 is a diagram showing a configuration of the information processing apparatus according to Embodiment 1.

Referring to FIG. 6, the information processing apparatus 3 includes a main body 300, an input unit 310, and a display unit 320. The main body 300 has a CPU 301, a ROM 302, a RAM 303, a hard disk 304, a reading device 305, an input/output interface 306, an image output interface 307, and a communication interface 308.

The CPU 301 executes a computer program stored in the ROM 302 and a computer program loaded in the RAM 303. The RAM 303 is used for reading the computer program recorded in the ROM 302 and the hard disk 304. The RAM 303 is also used as a work area of the CPU 301 when executing these computer programs.

In the hard disk 304, various computer programs to be executed by the CPU 301, such as operating systems and application programs, and data used for executing the computer programs is stored. Also, the measurement data received from the measuring device 2 is stored in the hard disk 304.

The hard disk 304 stores a program for measuring parameters for analysis including the number of immune cells contained in the sample, the cell size, the aspect ratio, the area showing fluorescence signals, the total fluorescence signal intensity in the area and the like, based on the measurement data, to analyze the sample, and a display program for displaying the analysis result on the display unit 320. By storing these programs, analysis processing and display processing described later are performed. That is, the CPU 301 is provided with a function of executing the processing of FIG. 7B described later by the programs.

The reading device 305 includes a CD drive, a DVD drive, and the like. The reading device 305 can read computer programs and data recorded on a recording medium such as a CD or a DVD.

The input unit 310 including a mouse, a keyboard and the like is connected to the input/output interface 306, and the user inputs an instruction to the information processing apparatus 3, using the input unit 310. The image output interface 307 is connected to the display unit 320 including a display and the like, and outputs a video signal corresponding to the image data to the display unit 320. The display unit 320 displays an image based on the inputted video signal.

The information processing apparatus 3 can receive the measurement data transmitted from the measuring device 2 through the communication interface 308. The received measurement data is stored in the hard disk 304.

Figure 7A:
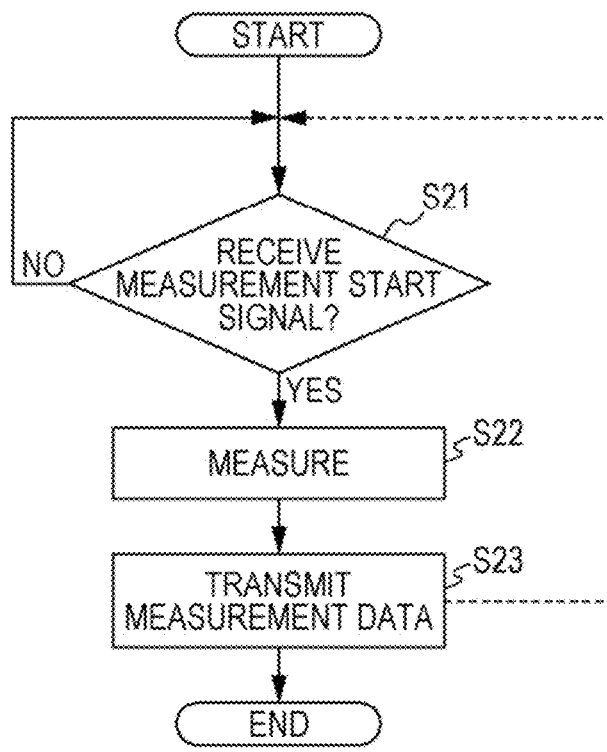
FIGS. 7A and 7B each depict flowcharts showing the measurement processing and the analysis processing of a specimen according to Embodiment 1.
Figure 7B:
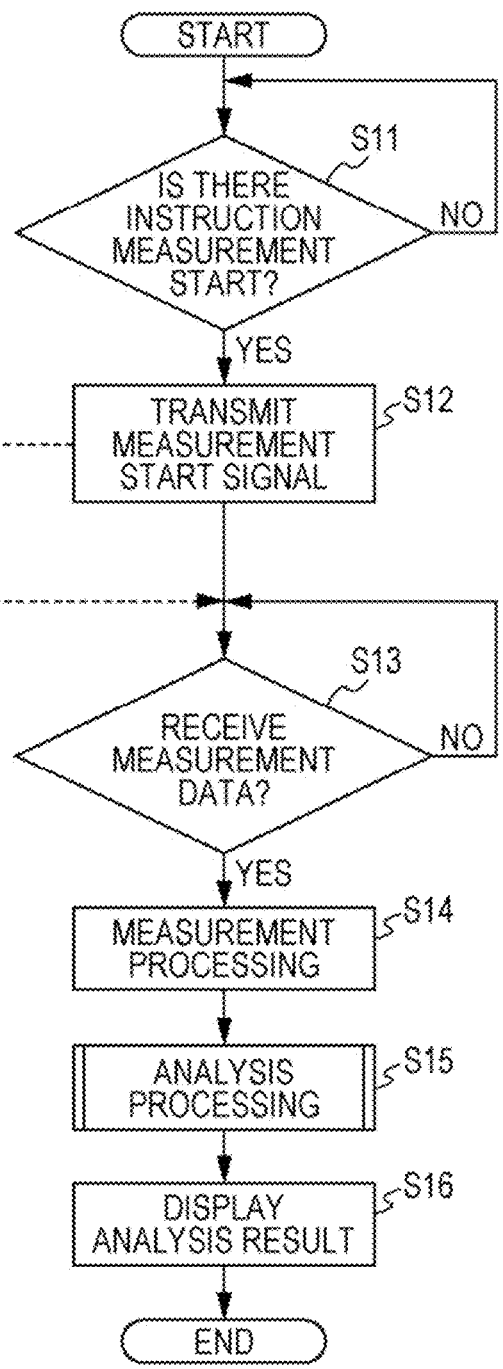

FIG. 7 is a flowchart showing the control of the CPU 204 of the measuring device 2 and the CPU 301 of the information processing apparatus 3. FIG. 7A is a flowchart showing control processing by the CPU 204 of the measuring device 2, and FIG. 7B is a flowchart showing control processing by the CPU 301 of the information processing apparatus 3.

Regarding the control processing of the CPU 301 of the information processing apparatus 3, refer to FIG. 7B. When a measurement start instruction is given from the user via the input unit 310 (step S11: YES), the CPU 301 transmits a measurement start signal to the measuring device 2 (step S12). Subsequently, the CPU 301 determines whether the measurement data has been received (step S13). When the measurement data has not been received (step S13: NO), the processing is on standby.

Regarding the control processing of the CPU 204 of the measuring device 2, refer to FIG. 7A. Upon receiving a measurement start signal from the information processing apparatus 3 (step S21: YES), the CPU 204 performs a measurement of the sample (step S22). In the measurement processing (step S22), a measurement sample including a complex of the capturing body and the immune cell is supplied together with a sheath liquid from the introduction unit 201 to the flow cell 203c, and a sample flow of the measurement sample enclosed in the sheath liquid is formed in the flow cell 203c. Laser beams from the light sources 203a, 203b are irradiated onto the formed sample flow, and a beam spot is formed on the flow cell 203c. When the immune cell passes through the beam spot, transmitted light and fluorescence are generated. The generated transmitted light and fluorescence are imaged by the camera 203i, respectively, and converted into electric signals.

These electric signals are converted into digital signals by the A/D converter 212, and subjected to signal processing by the digital signal processing unit 213. Thereby, measurement data including a transmitted light image and a fluorescence image is obtained for each complex that has passed through the flow cell 203c. The measurement data is stored in the memory 214. Upon completion of the measurement of the sample, the CPU 204 transmits the measurement data generated by the measurement processing to the information processing apparatus 3 (step S23), and ends the processing.

Again, refer to FIG. 7B. Upon receiving the measurement data from the measuring device 2 (step S13: YES), the CPU 301 of the information processing apparatus 3 stores the measurement data in the hard disk 304, and the CPU 301 performs analysis processing based on the measurement data (step S14). Subsequently, the CPU 301 displays the analysis result acquired in S14 on the display unit 320 (step S15). Thereafter, the processing ends.

Figure 10:
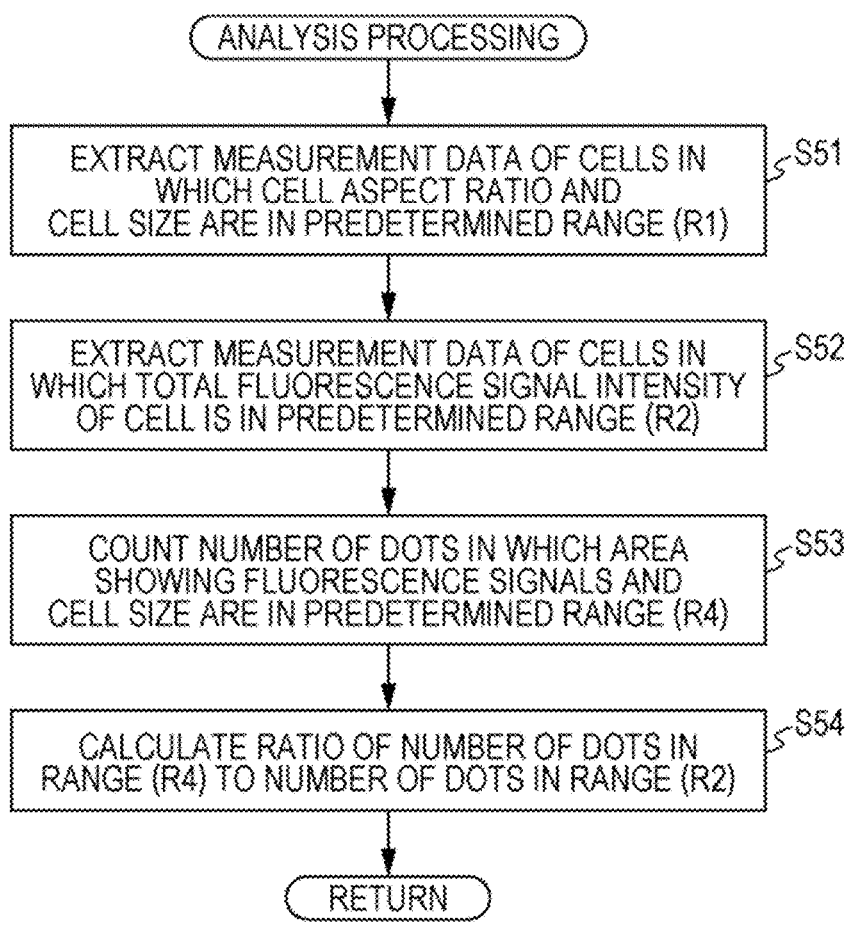
FIG. 10 is a flowchart showing the analysis processing according to Embodiment 1.

With reference to FIGS. 8 to 10, an example of the analysis processing (step S14 in FIG. 7B) performed by the CPU 301 of the information processing apparatus 3 based on the measurement data will be further described. FIGS. 8A and 8B show transmitted light images, fluorescence images (CD28) and superimposed images thereof, among the measurement data obtained by measuring the immune cells. As shown by the fluorescence image in FIG. 8A, when immune stimulation is not given, costimulatory molecules CD28 tend to be uniformly distributed on the cell membrane of the immune cell. As shown by the fluorescence image in FIG. 8B, when immune stimulation is given, costimulatory molecules CD28 tends to localize in a part of the cell membrane of the immune cell. Although not intending to be bound by theory, it is considered that the cell membrane part where the costimulatory molecules are localized is a contact surface between the immune cell and a substance different from the immune cell, formed on the immune cell. That is, it is considered that the part where the costimulatory molecules are localized indicates an immune synapse formed between this cell and a substance different therefrom.

The CPU 301 measures parameters for analysis based on the transmitted light images and fluorescence images of all the cells imaged in step S22 of FIG. 7A (step S14 in FIG. 7B). Parameters for analysis include, but are not limited to, cell size (the number of pixels), cell aspect ratio, area (the number of pixels) showing the fluorescence signals in the cell, total fluorescence signal intensity (total fluorescence signal intensity of the cell) within the area, and a ratio thereof. FIG. 9 is a schematic diagram of measurement processing of the transmitted light image and fluorescence image (step S14 in FIG. 7B) shown in FIG. 8B by the CPU 301 of the information processing apparatus 3. The resulting measurement data is stored in the hard disk 304. The meanings of each term of the cell size, aspect ratio, area showing fluorescence signals, and total fluorescence signal intensity are as described above.

FIG. 10 is a flowchart showing the analysis processing in step S15 of the CPU 301 of the information processing apparatus 3. The CPU 301 generates a two-dimensional histogram (2D scattergram) in which the parameters for analysis measured in step S14 are assigned to the X axis and the Y axis, respectively, and the CPU 301 extracts and analyzes the measurement data of the cells corresponding to the dots present within the predetermined range.

Figure 11A:
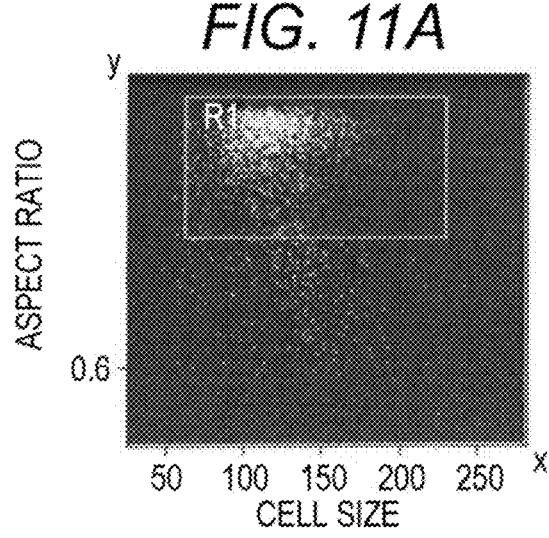
FIGS. 11A, 11B, 11C, and 11D are 2D scattergrams showing the analysis processing according to Embodiment 1 (FIGS. 11A, 11B and 11C) and Embodiment 2 (FIG. 11D)

In this embodiment, the CPU 301 firstly generates a 2D scattergram in which the cell size is assigned to the X axis and the cell aspect ratio is assigned to the Y axis (FIG. 11A), and the CPU 301 extracts the measurement data of the cells in the predetermined range (R1) (step S51). The range (R1) is gated in a predetermined range reflecting the size of the cell alone in the cell size (X axis), and the range (R1) is gated in a predetermined range reflecting that the cell is present alone in the aspect ratio (Y axis). Thereby, the data derived from substances such as cell pieces smaller than a cell and from cell aggregates larger than a cell alone is excluded.

Each one of the dots displayed on the 2D scattergram indicates the measurement value of individual cell. The CPU 301 extracts the measurement data of the cell indicating the measurement value in the region displayed as R1 in the image. In this embodiment, the measurement data of individual cells measured in step S22 of FIG. 7A is linked to the dot displayed on the 2D scattergram. When the user designates a dot displayed on the 2D scattergram, the CPU 301 reads from the hard disk 304 the measurement data (transmitted light image and/or fluorescence image) of the cell corresponding to the dot, and the CPU 301 displays it on the display unit 320.

With respect to the measurement data of the cell extracted in step S51, the CPU 301 generates a 2D scattergram in which the total fluorescence signal intensity of the cell is assigned to the X axis and the sharpness of the fluorescence image (sharpness of the image) is assigned to the Y axis (FIG. 11B), and the CPU 301 further extracts the measurement data of the cells in the predetermined range (R2) (step S52). The range (R2) is gated in a range reflecting the expression level of a predetermined amount of costimulatory molecules CD28 on the total fluorescence signal intensity (X axis) of the cell, and the range (R2) is gated in a range reflecting the sharpness of the predetermined image in sharpness (Y axis). As a result, data of cells expressing a predetermined amount of costimulatory molecules CD28 is extracted, and data of cells not expressing a predetermined amount of costimulatory molecules CD28 is excluded.

Subsequently, with respect to the measurement data of the cell extracted in step S52, the CPU 301 generates a 2D scattergram in which the area showing fluorescence signals assigned to the X axis and the size of the cell assigned to the Y axis (FIG. 11C), and the CPU 301 counts the number of dots in the predetermined range (R4) (step S53). The range (R4) is gated in a predetermined range reflecting the localization of costimulatory molecules CD28 in the area (X axis) showing fluorescence signals, and the range (R4) is gated in a predetermined range reflecting the size of the cell alone in the cell size (Y axis). By counting the number of dots in the range (R4), the number of immune cells having a response to immune stimulation is counted. In this embodiment, cells corresponding to the dots in the range (R4) tend to have immune synapses formed, and the cells are determined to have a response to the immune stimulation in this embodiment.

Figure 11B:
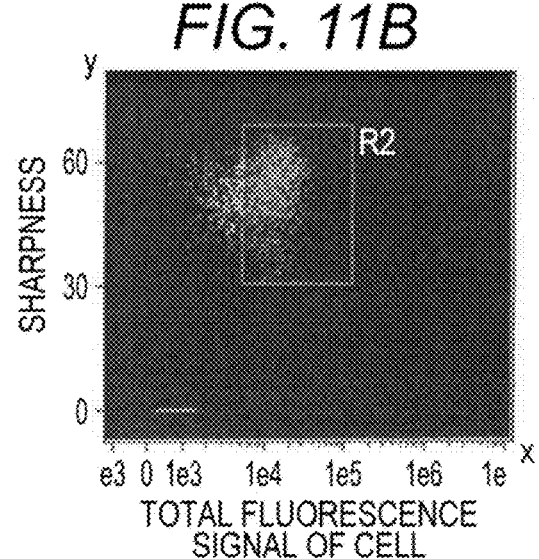
Figure 11C:
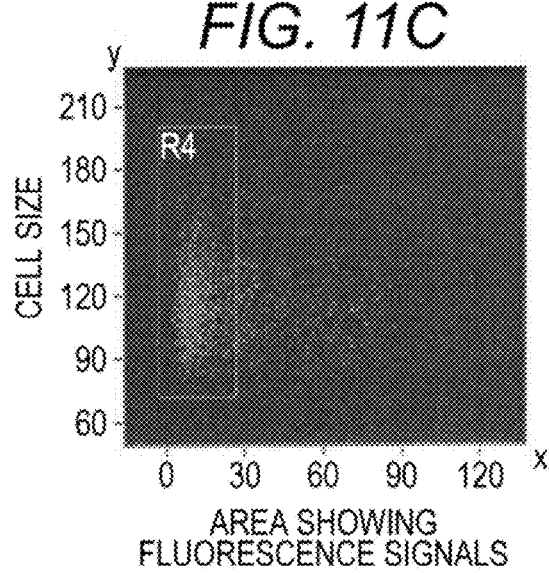

The CPU 301 further counts the number of dots shown in entire FIG. 11C (corresponding to the number of dots in the range (R2) in FIG. 11B), and the CPU 301 calculates the ratio of the number of dots in the range (R4) to the number of dots in the range (R2) ([the number of dots in the range (R4)]/[the number of dots in the range (R2)]) (step S54). Thereby, the proportion of immune cells having an immunostimulatory response, among individual immune cells expressing a predetermined amount of costimulatory molecules CD28 is calculated.

The analysis results on the number of dots and the ratio within each range obtained by the above analysis processing are displayed on the display unit 320.

The analysis results may be further analyzed, for example, by comparing with the proportion of immune cells having an immunostimulatory response standardized for a biological sample derived from a healthy subject. In this further analysis, for example, when the proportion of the sample is higher than the standardized proportion, the sample can be determined to have a high immunological response. Alternatively, the analysis results may be further analyzed by comparing with the proportion of immune cells having an immunostimulatory response for a previous biological sample derived from the same subject. In this further analysis, for example, when the proportion of the sample is higher than the previous proportion, the subject may be determined to have an improved immunological response.

Thus, in one embodiment, there is provided a cell analyzer including an introduction unit for introducing a complex of an immune cell and a capturing body that binds to a surface antigen of the immune cell and is capable of generating an optical signal, an imaging unit for imaging the complex supplied from the introduction unit, and an analyzing unit for determining whether or not the immune cell has an immunostimulatory response, based on the image captured by the imaging unit. In a specific embodiment, the analyzing unit acquires a value reflecting a distribution of surface antigens, based on the image, and compares the acquired value with a threshold value, thereby determining whether or not the immune cell has an immunostimulatory response. In other embodiment, there is provided a cell analyzer in which the capturing body includes a fluorescent substance, the image includes a fluorescence image, the value reflecting the distribution of surface antigens includes an area showing fluorescence signals that reflects the distribution of surface antigens based on the fluorescence image, and when the area is smaller than the threshold value, the immune cell is determined to have the immunostimulatory response. In other embodiment, there is provided a cell analyzer in which the image includes a transmitted light image, and the analyzing unit acquires a value reflecting the size of the immune cell based on the transmitted light image and determines whether or not the immune cell has an immunostimulatory response, based on the value reflecting the size of the immune cell and the value reflecting the distribution of surface antigens.

The analysis processing described above is merely an example of analysis processing based on measurement data, and different analysis processing can be used.

Embodiment 2 of Cell Analyzer

In place of the step S53 of the analysis processing of Embodiment 1, with respect to the measurement data extracted in step S52, the CPU 301 may generate a 2D scattergram in which the total fluorescence signal intensity of the cell is assigned to the X axis and the area showing fluorescence signals is assigned to the Y axis (FIG. 11D), and the CPU 301 may count the number of measurement data in the predetermined range (R3). The range (R3) is gated in a range reflecting a predetermined expression level of costimulatory molecules CD28 per cell in the total fluorescence signal intensity (X axis) of the cell, and the range (R3) is gated in a predetermined range reflecting the localization of costimulatory molecule CD28 in the area (Y axis) showing fluorescence signals. By counting the measurement data in the range (R3), the number of immune cells responsive to immune stimulation is counted. In this embodiment, cells corresponding to the dots in the range (R3) tend to have immune synapses formed, and the cells are determined to have a response to the immune stimulation in this embodiment.

Figure 11D:
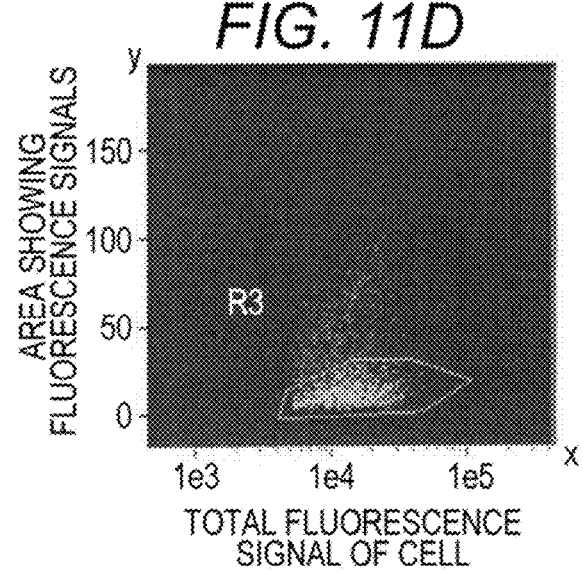

In this embodiment, in place of step S54, the CPU 301 may further count the number of dots shown in entire FIG. 11D (corresponding to the number of dots in the range (R2) in FIG. 11B), and the CPU 301 may calculate the ratio of the number of dots in the range (R3) to the number of dots in the range (R2) ([the number of dots in the range (R3)]/[the number of dots in the range (R2)]). Thereby, the proportion of immune cells having an immunostimulatory response, among individual immune cells expressing a predetermined amount of costimulatory molecules CD28 is calculated.

Embodiment 3 of Cell Analyzer

In place of the step S53 of the analysis processing of Embodiment 1, with respect to the measurement data of the cell extracted in step S52, the CPU 301 may generate a histogram in which the class value for the area showing fluorescence signals is assigned to the X axis and the frequency is assigned to the Y axis, and the CPU 301 may display it on the display unit 320. The CPU 301 may further calculate the average value, the median value, and the most frequent value of the area showing fluorescence signals of the measurement data extracted in step S52 from this histogram, in place of step S54. The resulting mean value, median value and most frequent value may be further analyzed by comparing with standardized mean value, median value and most frequent value of the area showing fluorescence signals in immune cells, obtained from a biological sample derived from a healthy subject. In this further analysis, for example, when a class value (area showing fluorescence signals) indicating the most frequent value of the sample is smaller than a class value (area showing fluorescence signals) indicating the standardized most frequent value, this suggests that the costimulatory molecule CD28 is localized, and consequently the sample may be determined to have a high response to immune stimulation.

As shown in Embodiment 3, it is possible to analyze the immunological response of immune cells even without creating a 2D scattergram in the analysis of measurement data. However, as described in Embodiment 1, the measurement data of individual immune cell can be linked to the dot shown in the 2D scattergram, and for example, the measurement data including a transmitted light image and a fluorescence image of the immune cell can be displayed by designating each dot. Therefore, the analysis by the 2D scattergram is a preferable analysis processing method in that detailed analysis based on the image can be additionally performed on individual cell.

Embodiment 4 of Cell Analyzer

In the above analysis processing, the analysis based on the imaged image data is exemplified, but the immunostimulatory response of immune cells can also be analyzed from measurement data other than the imaged image data. For example, in the measuring device 2 (FIG. 4) in Embodiment 1, the dichroic mirrors 203*j* and 203*k*, a forward scattered light receiving section 203*l* and a fluorescence receiving section 203*m* are used, in place of the optical unit 203*g* and the camera 203. The light of wavelength λ1 irradiated from the light source 203*a* is irradiated onto the sample passing through the inside of the flow cell 203*c*, whereby forward scattered light of wavelength λ1 is generated from the immune cell. The light of wavelength λ2 irradiated from the light source 203*b* is irradiated onto the sample passing through the inside of the flow cell 203*c*, whereby fluorescence of wavelength λ3 is generated from PE. The sample in Embodiment 4 is the complex used in Embodiment 1. The forward scattered light of wavelength λ1 is reflected by the dichroic mirror 203*j* and received by the forward scattered light receiving section 203*l*. The fluorescence of wavelength λ3 passes through the dichroic mirror 203*j*, is reflected by the dichroic mirror 203*k* and is received by the fluorescence receiving section 203*m*. The forward scattered light receiving section 203*l* and the fluorescence receiving section 203*m* are photomultipliers. In this example, the optical signal obtained in step S22 of FIG. 7A is a forward scattered light signal and fluorescence signal, and in step S14 of FIG. 7B, "pulse width (w)", "pulse area (A)" and "pulse height (H)" are obtained as parameters for analysis. These parameters for analysis will be described with reference to FIG. 12.

FIGS. 12A to 12D are schematic diagrams, by way of example, showing fluorescence signals detected while the cells in which costimulatory molecules CD28 are uniformly distributed on the cell membrane (FIG. 12A) and the cell in which costimulatory molecules CD28 are localized on the cell membrane (FIG. 12B) pass through the region detecting fluorescence signal (not shown) in the direction of the arrows (FIGS. 12C and 12D), respectively.

Figure 12A:
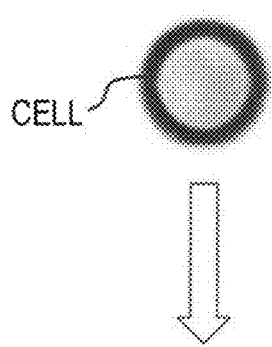
FIGS. 12A, 12B, 12C, and 12D are schematic diagrams for describing pulse data of fluorescence signals obtained from cells having different distribution states of costimulatory molecules.
Figure 12B:
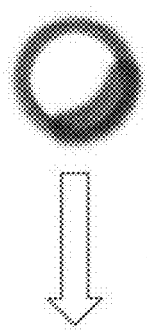
Figure 12C:
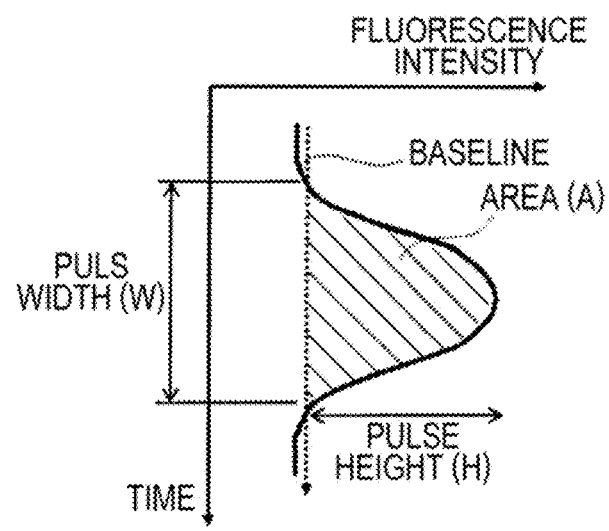
Figure 12D:
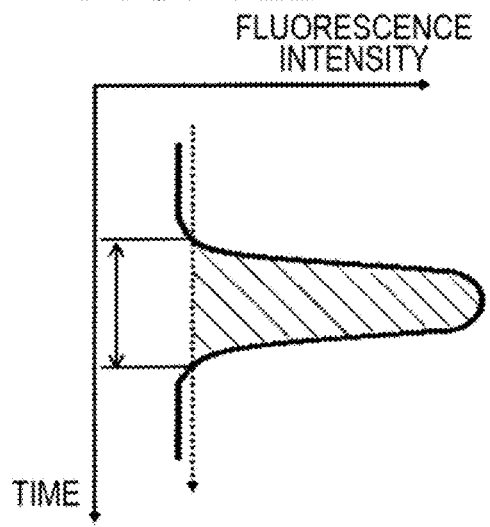

As used herein, in the pulse of the fluorescence intensity as shown in FIGS. 12C and 12D, the time when the fluorescence signal is obtained beyond the baseline as a threshold value is referred to as "pulse width (w)", and the fluorescence intensity in the case of showing the pulse peak in the fluorescence intensity is referred to as "pulse height (H)". "Pulse area (A)" refers to the area between the baseline and the fluorescence signal intensity curve.

In this example, the same amount of costimulatory molecules CD28 is expressed on the cell membrane in the cells of FIG. 12A and the cells of FIG. 12B, and the pulsed area (A) of FIGS. 12C and 12D are equal. The pulse width (w) and pulse height (H) are different according to the distribution pattern of costimulatory molecules. The pulse width (w) is narrowed when the costimulatory molecules are localized on the cell membrane (FIG. 12B) as compared with the case where the costimulatory molecules are uniformly distributed on the cell membrane (FIG. 12A), whereas the pulse height (H) increases (FIGS. 12C and 12D).

Figure 13A:
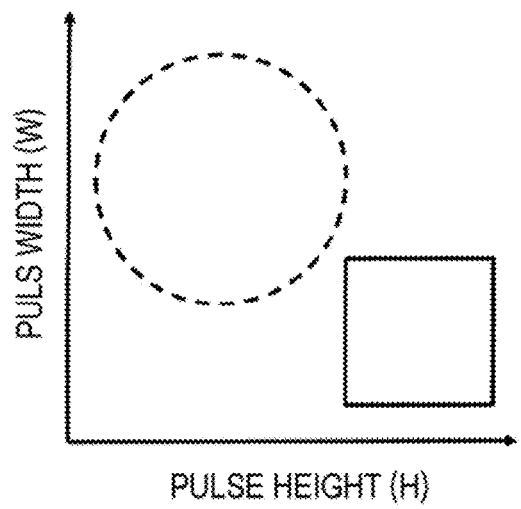
FIGS. 13A and 13B are schematic diagrams for describing 2D scattergrams of parameters for analysis obtained from pulse data of fluorescence signals.
Figure 13B:
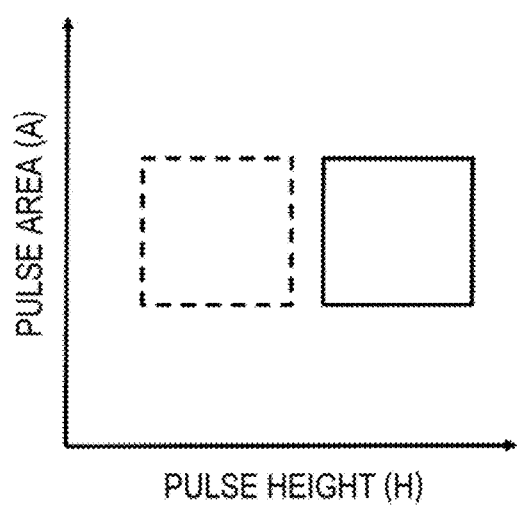

FIGS. 13A and 13B are schematic diagrams in the case of preparing 2D scattergrams by measuring a plurality of immune cells in this embodiment. FIG. 13A is a 2D scattergram in which the pulse height (H) is assigned to the X axis and the pulse width (w) is assigned to the Y axis, and FIG. 13B is a 2D scattergram in which the pulse height (H) is assigned to the X axis and the pulse area (A) is assigned to the Y axis.

As described above, when the costimulatory molecules are uniformly distributed on the cell membrane (FIG. 12A), the pulse width (w) shows a tendency to spread and the pulse height (H) shows a tendency to be lower (FIGS. 12C and 12D), as compared with the case where the costimulatory molecules are localized on the cell membrane (FIG. 12B). Therefore, in the 2D scattergram shown in FIG. 13A, the data in the region surrounded by a dashed circle tend to show data reflecting the cells in which costimulatory molecules are uniformly distributed on the cell membrane, whereas the data in the region surrounded by a solid line square tend to show data reflecting the cells in which costimulatory molecules are localized on the cell membrane. In the 2D scattergrams shown in FIG. 13B, the data in the region surrounded by a dashed square tend to show data reflecting the cells in which costimulatory molecules are uniformly distributed on the cell membrane, whereas the data in the region surrounded by a solid line square tend to show data reflecting the cells in which costimulatory molecules are localized on the cell membrane.

Thus, in one embodiment, there is provided a cell analyzer including an introduction unit for introducing a complex of an immune cell and a capturing body that binds to a surface antigen of the immune cell and is capable of generating an optical signal, a detection unit for irradiating the complex supplied from the introduction unit with light and detecting the generated optical signal from the complex, and an analyzing unit for determining whether or not the immune cell has an immunostimulatory response, based on the detected optical signal. In a specific embodiment, there is provided a cell analyzer in which the capturing body includes a fluorescent substance, the detection unit detects a fluorescence signal generated from the complex, and the analyzing unit acquires a value reflecting the distribution of surface antigens, based on the fluorescence signal, and compares the acquired value with a threshold value, thereby determining whether or not the immune cell has an immunostimulatory response, and the value reflecting the distribution of surface antigens includes at least one of a pulse width, a pulse height and a pulse area of the fluorescence signal from the complex.

As shown in Examples, the cell in which the surface antigen to which the capturing body is bound or the costimulatory molecules are localized on the cell membrane is determined to be an immune cell exhibiting an immunological response. Thus, in FIGS. 13A and 13B, the cells that show data in the region surrounded by a solid line square can be determined to be cells exhibiting an immunological response. As exemplified in this embodiment, it is understood that an immune cell having the immunostimulatory response can be measured not only by analysis processing based on imaged image data but also by the above-described analysis processing.

The parameters for analysis and the analysis processing shown here are merely examples, and different parameters for analysis may be measured from the measurement data, or different analysis processing may be performed on the measured parameters for analysis. For example, the pulse area may be an approximate value as long as it reflects the area under the time curve of the pulse, and is not limited to the time integral value. The pulse area may be the product of the pulse width and the height of the peak, or may be the area of a triangle obtained from the pulse width and the height of the peak. In addition, in the mode of measuring the time integral value, the base may not be the baseline and can be set appropriately. For example, a value exceeding a predetermined threshold value from the baseline may be used as the base.

Hereinafter, specific examples will be described, which show preferred embodiments and do not limit the invention defined in the appended claims in any way. Equivalents that are easily recognized from the specific embodiments, materials, compositions and methods described herein, or changes, alterations or modifications are intended to be within the scope of the present disclosure.

EXAMPLES

Example 1: Measurement of Immunostimulatory Response of Immune Cells Using CD28 as Index (1) Preparation of Clonal T Cells $5\times10^6$ CD4 positive cells (Stemcell Technologies: ST-70026) and CD8 positive cells (Funakoshi: 0508-100, COSMO BIO: PB08C-1) were seeded in Yssel's medium (Gemini Bio-Products: 400102) added with 1 µg/mL LEAF (trademark) Purified anti-human CD3 Antibody (Biolegend: 317315), 10 ng/mL of Recombinant human IL-2 (rhIL-2) (R&D systems: 202-IL-500), 0.2 µg/mL of Phytohemagglutinin-L (PHA) (SIGMA: L4144-5MG) and 2% human serum (SIGMA: H4522-100ML), and co-cultured with $1\times10^6$ peripheral blood mononuclear cells and $1\times10^4$ JY cells for 14 days. Fourteen days later, T cells were seeded in 96-well plates so as to be 0.3, 1.0 and 3.0 cells/well by limiting dilution, and cultured until colonies with $1\times10^4$ peripheral blood mononuclear cells were formed. The T cells were recovered from the colonized wells to obtain clonal T cells. Hereinafter, the obtained T cells are also referred to as "prepared clonal T cells".

(2) Immobilization of Antibodies

300 µl of a solution (0.01 mg/ml) of anti-CD3 antibody (BioLegend #300414 Clone: UCHT1) was added to 24-well plate per well to immobilize the anti-CD3 antibody on the well surface. Hereinafter, the resulting plate is also referred to as "anti-CD3 antibody immobilized plate".

(3) Stimulation and Measurement of Immune Cells

The prepared clonal T cells were added to the anti-CD3 antibody-immobilized plate to give about $5\times10^5$ cells per well. Then, anti-CD28 antibody (BioLegend #302914 Clone: CD28.2) was added to the cells in the well so as to have a final concentration of 0.01 mg/ml. The plate was centrifuged (200 G, 30 seconds) and then incubated at 37° C. for 30 minutes. The prepared clonal T cells were recovered from the well surface by pipetting. The recovered T cells were immobilized using a fixing solution containing 1% paraformaldehyde (PFA). The immobilized T cells were immunostained using PE-labeled anti-mouse IgG antibody (BioLegend #405307). The stained T cells ($5\times10^5$ cells/20 µl) were measured using Imaging FCM (ImageStreamX Mark II Imaging Flow Cytometer: Amnis).

For comparison, the cases where cells were not immunostimulated by contact with antibodies that bind to T cell surface antigens (anti-CD28 antibody and anti-CD3 antibody) and contact with different substances (wells of plate) were also examined. The clonal T cells prepared in the above (1) were fixed using the fixing solution described above without performing the above-described immune stimulation, and then stained using an anti-CD28 antibody. The fixed T cells were secondarily stained using PE-labeled anti-mouse IgG antibody, and measured.

Figure 14A:
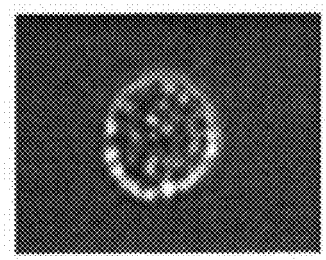
FIGS. 14A and 14B are transmitted light images, fluorescence images and superimposed images thereof showing the distribution of CD28 in T cells in the case without stimulation (FIG. 14A) and the case with stimulation (FIG. 14B)
Figure 14B:
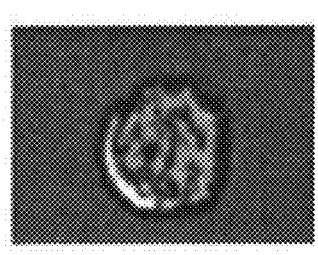

When the immune stimulation was not given to the T cells, CD28 was uniformly distributed on the cell membrane in the T cells (see FIG. 14A). When the immune stimulation was not given and then the contact surface between the T cell and the well was eliminated, CD28 showed localization on the cell membrane of T cells (see FIG. 14B). As described above, even when the immune stimulation was given and then the contact surface between the T cell and the well was eliminated, immune synapse could be detected by using the costimulatory molecule CD28 as an index.

(4) Data Analysis

Figure 15A:
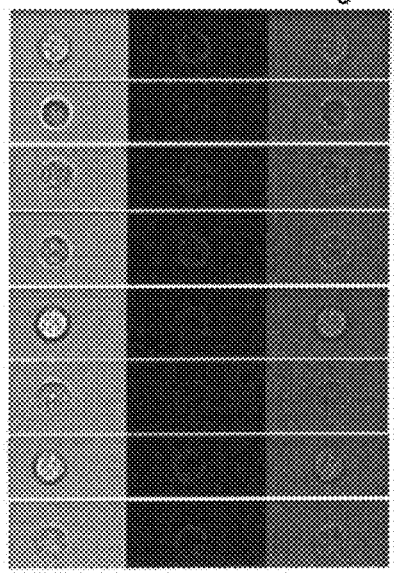
FIGS. 15A, 15B, 15C, and 15D are images and 2D scattergrams showing the distribution of CD28 in T cells. Differential interference images (DIC), fluorescence images (CD28) of T cells and superimposed images thereof (Merge) in the case without stimulation (FIG. 15A) and the case with stimulation (FIG. 15C). 2D scattergrams showing the area showing fluorescence signals in the cell (X axis) and cell size (Y axis) in the case without stimulation (FIG. 15B) and the case with stimulation (FIG. 15D)
Figure 15C:
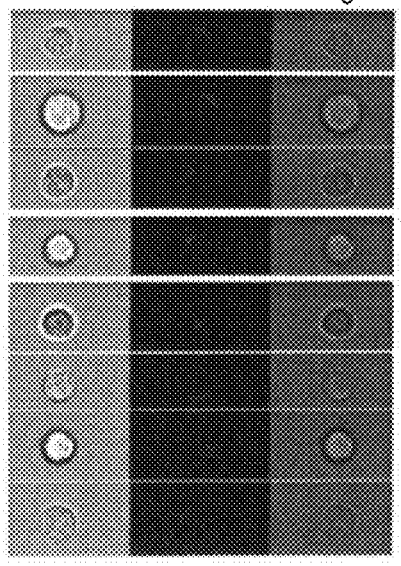
Figure 15B:
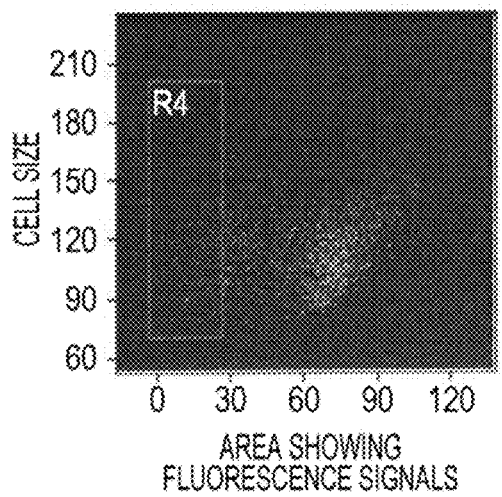

Multiple parameter analysis of the measurement data (FIGS. 15A and 15B) of the sample containing T cells without immune stimulation and the measurement data (FIGS. 15C and 15D) of the sample containing T cells with immune stimulation obtained by measurement using Imaging FCM was performed.

Detailed measurement processing and analysis processing were shown in Embodiment 1. Briefly, images were analyzed based on the transmitted light image and the fluorescence image (CD28) measured using Imaging FCM (FIG. 9), and the cell size (the number of pixels), the cell aspect ratio, the area (the number of pixels) showing the fluorescence signals in the cell and the total fluorescence signal intensity (total fluorescence signal intensity of the cell) within the area were measured. First, a 2D scattergram in which the cell size was assigned to the X axis and the cell aspect ratio was assigned to the Y axis was generated, and the measurement data of the cells corresponding to dots in the predetermined range (R1) was extracted (step S51 in FIG. 10). Next, for the measurement data in the range (R1), the measurement data corresponding to dots in which the total fluorescence signal intensity of the cell is in the predetermined range (R2) was further extracted (step S52 in FIG. 10). For the measurement data in the range (R2), the numbers of dots in the regions displayed as R4 (FIGS. 15B and 15D) were counted, respectively (step S53 in FIG. 10). Also, the numbers of dots on the scattergrams of FIGS. 15B and 15D (the number of dots in the range (R2)) were counted. Then, the ratios of the number of dots in the range (R4) to the number of dots in the range (R2) were calculated by the following equation (1) (step S54 in FIG. 10). The results are summarized in Table 1 below.

$$[\text{Ratio}(R4/R2)] = \{[\text{Number of dots in range}(R4)] / [\text{Number of dots in range}(R2)]\} \times 100 \quad \text{Equation (1)}$$

TABLE 1

| Analysis processing step | Without immune stimulation (FIGS. 15A and 15B) | With immune stimulation (FIGS. 15C and 15D) |
| --- | --- | --- |
| S52 Range (R2) [count] | 1503 | 2219 |
| S53 Range (R4) [count] | 138 | 1799 |
| S54 Proportion (R4/R2) [%] | 9.2 | 81.1 |

According to the examples of the present specification, it was found that when immune synapse that can be formed when immune stimulation including contact with immunostimulators and contact surface formation with a different substance are given to immune cells is detected using a costimulatory molecule as an index, information on immunological response of the immune cells is accurately obtained, even when the contact surface is not maintained. This was a surprising result, given that the immune synapse is a loose bond formed in the immune cell on the surface connected with the target cell.

Thus, according to the invention of the present application, an immunostimulatory response of immune cells can be measured on the basis of immune synapses, so that it is understood that the activation state of immune cells can be measured more quickly and easily than the conventional method for analyzing the response of immune cells based on cytokine production.

In the examples of the present specification, the immunostimulatory response of immune cells can be measured using an imaging flow cytometer could be measured, it was demonstrated that a large number of cells can be measured, and statistically highly accurate measurement of immunological response is possible. In the above example, the immunostimulatory response of immune cells was measured using an imaging flow cytometer, but it is understood that it can be also measured by an imaging cytometer capable of measuring a large number of cells, similarly to the measuring device used in the examples. Further, as described in Embodiment 4, it is understood that the immunostimulatory response of a large number of immune cells can be also measured by a non-imaging flow cytometer, similarly to the measuring device used in the examples. Thus, it is understood that, since the activation state of immune cells can be quickly and easily measured in a large number of cells according to the invention of the present application, it is useful for statistically highly accurate evaluation of drug efficacy.

Figure 15D:
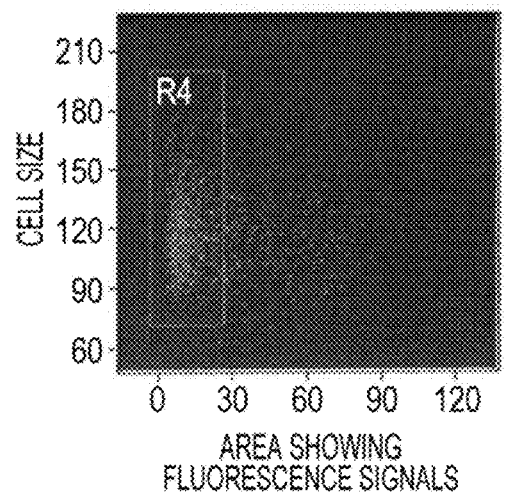

In the above example, since an imaging flow cytometer is used, image data of individual cells can be linked to each measurement data in the analysis of measurement data of each cell. Therefore, based on the measurement data, a predetermined analysis processing is performed to select cells, based on the measurement data, then the image data of the cells is further combined, whereby the immunostimulatory response can be evaluated. For example, about 81% of the cells in the range (R4) were present in the samples with immune stimulation in the analysis processing for selecting cells with a high tendency to form an immune synapse in the above example (Table 1). In FIG. 15D, the image data of the cells is displayed by designating the dots corresponding to cells in the range (R4), and the image data is evaluated together, whereby the response of immune cells to immune stimulation can be further evaluated. As with the imaging flow cytometer, it is understood that this further evaluation can be evaluated also by an imaging cytometer for imaging images of cells.

According to the measuring method and the cell analyzer, it is effective so as to quickly and easily evaluate, for example, the activation state of immune cells in the body of a subject related to cancer immunity, autoimmune disease or the like in the case of using an immunostimulatory antibody as the immunostimulator, the activation state of immune cells in the body of a subject related to infectious disease, allergic disease or the like in the case of using a specific antigenic peptide, and in addition, immunological response of a subject for transplantation therapy and regenerative therapy in the case of using an allogenic cell or allogenic MHC. As described above, it is understood that imaging flow cytometer and imaging cytometer that can further utilize the image data of individual cells for the analysis processing have further advantages.

Reference Example: Correlation Between Immune Synapse Formation and Cytokine Production in Immune Cells (1) Measurement of Cytokine-Producing Cells In the same manner as in Example 1, the anti-CD3 antibody was immobilized on each well of the plate to prepare an anti-CD3 antibody-immobilized plate. Also, in the same manner as in Example 1, clonal T cells were prepared from human peripheral blood. The clonal T cells were added to the anti-CD3 antibody-immobilized plate to give about $5 \times 10^5$ cells per well. Then, anti-CD28 antibody (BioLegend #302914 Clone: CD28.2) was added to the cells in the well so as to have a final concentration of 0.01 mg/ml, and incubated at 37° C. for 4 hours. Thereafter, Brefeldin A was added to each well so as to have a final concentration of 10 μg/ml, and incubated for 2 hours. Then, the plate was allowed to stand on ice, and the cells in each well were recovered. The recovered T cells were fixed with a fixing solution containing 1% PFA and then subjected to a membrane permeation treatment with a PBS solution containing 0.5% saponin and 1% BSA. The treated cells were immunostained using Alexa Fluor (registered trademark) 488 labeled anti-IFN-γ antibody (BioLegend #502517 Clone: 4S.B3). The stained T cells were measured with a flow cytometer (BD biosciences: Accuri (trademark)). The measurement data was analyzed by a conventional method to acquire the proportion of IFN-γ positive cells in the measured T cells.

(2) Measurement of Cells that Formed Immune Synapse

T cells seeded from the same well as the T cells used in (1) above were used to measure the cells that formed immune synapse using CD28 as an index. The measurement data was analyzed to acquire the proportion of cells that formed immune synapse in the measured T cells. Measurement and data analysis were performed in the same manner as in Example 1.

(3) Results

Figure 16:
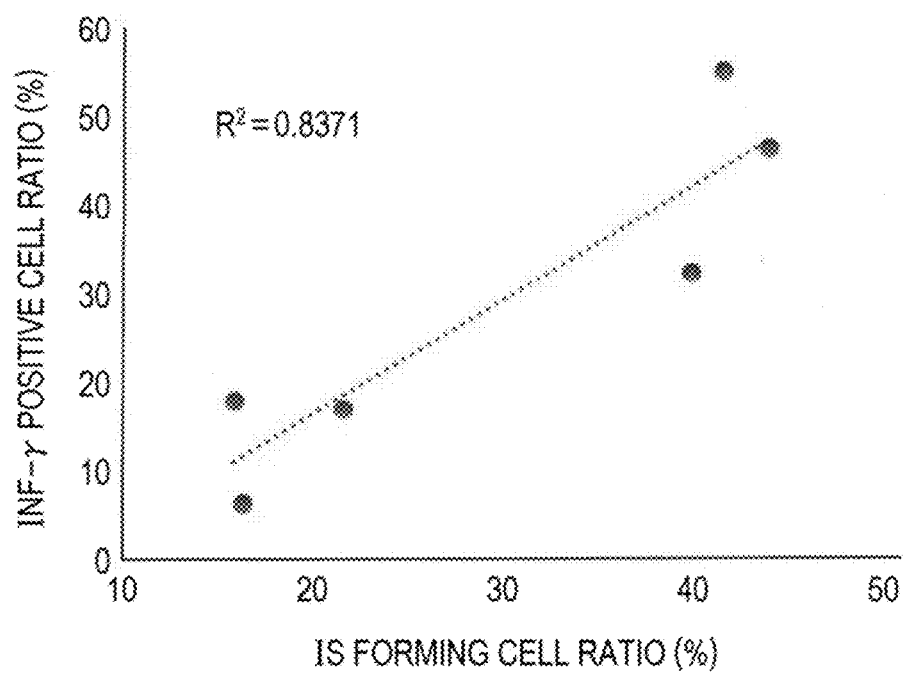
FIG. 16 is a graph showing the correlation between cytokine secretion and immune synapse formation in T cells.
Figure 18A:
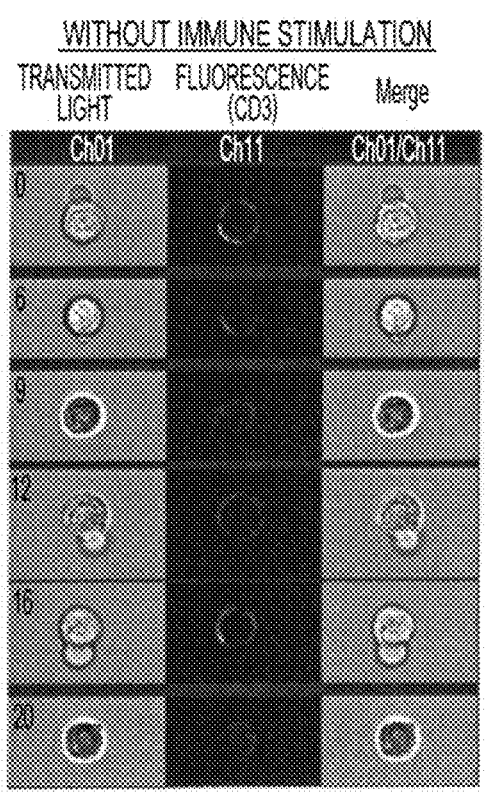
FIGS. 18A, 18B, 18C, and 18D are images and 2D scattergrams showing the distribution of CD3 in T cells. Transmitted light images, fluorescence images of T cells and superimposed images thereof (Merge) in the case without stimulation (FIG. 18A) and the case with stimulation (FIG. 18C). 2D scattergrams showing the total fluorescence signal intensity of the cell (X axis) and the area showing fluorescence signals (Y axis) in the case without stimulation (FIG. 18B) and the case with stimulation (FIG. 18D)
Figure 18C:
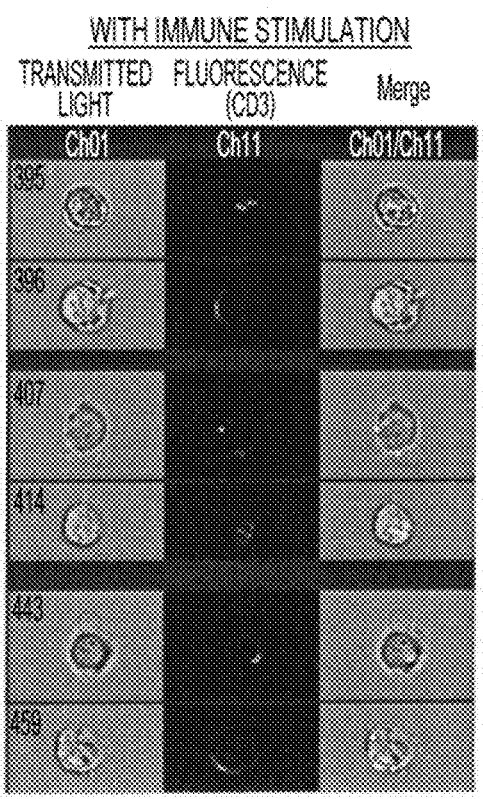
Figure 18B:
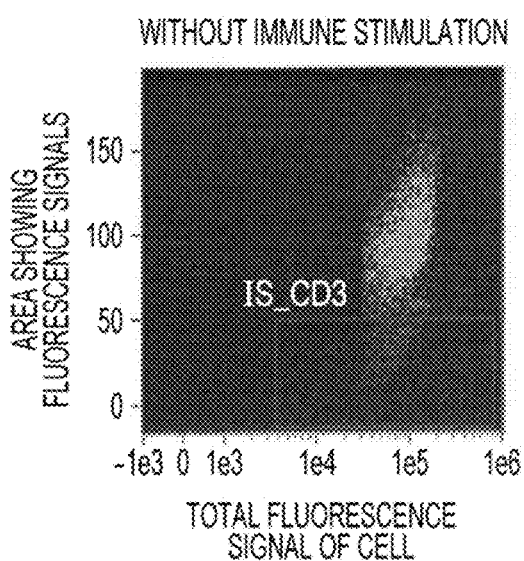
Figure 18D:
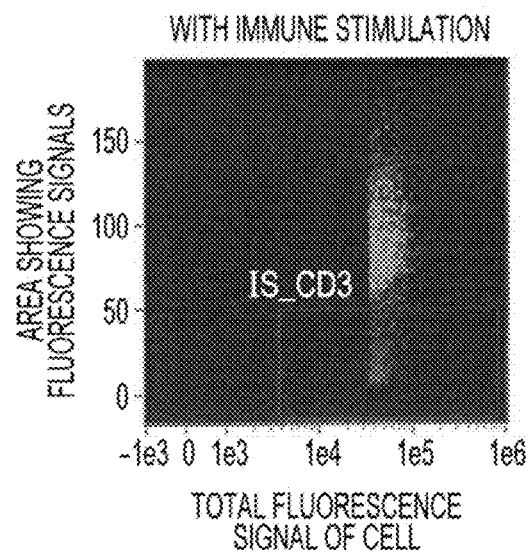
Figure 19A:
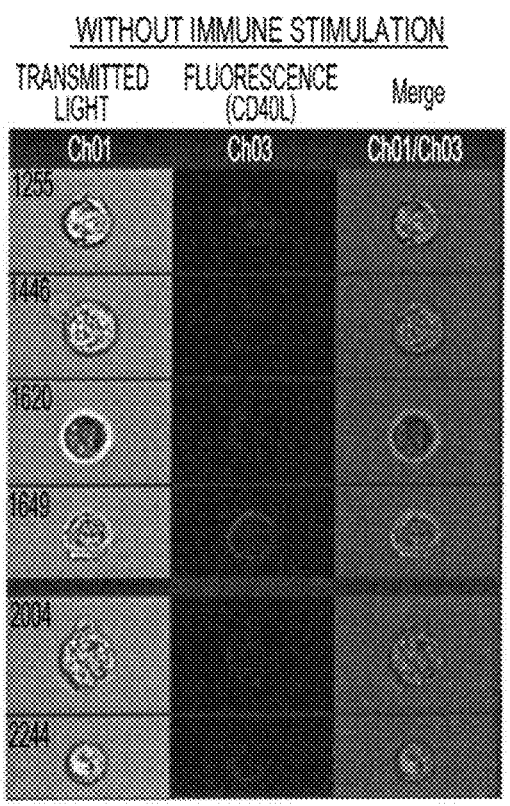
FIGS. 19A, 19B, 19C, and 19D are images and 2D scattergrams showing the distribution of CD40L in T cells. Transmitted light images, fluorescence images of T cells and superimposed images thereof (Merge) in the case without stimulation (FIG. 19A) and the case with stimulation (FIG. 19C). 2D scattergrams showing the total fluorescence signal intensity of the cell (X axis) and the area showing fluorescence signals (Y axis) in the case without stimulation (FIG. 19B) and the case with stimulation (FIG. 19D)
Figure 19C:
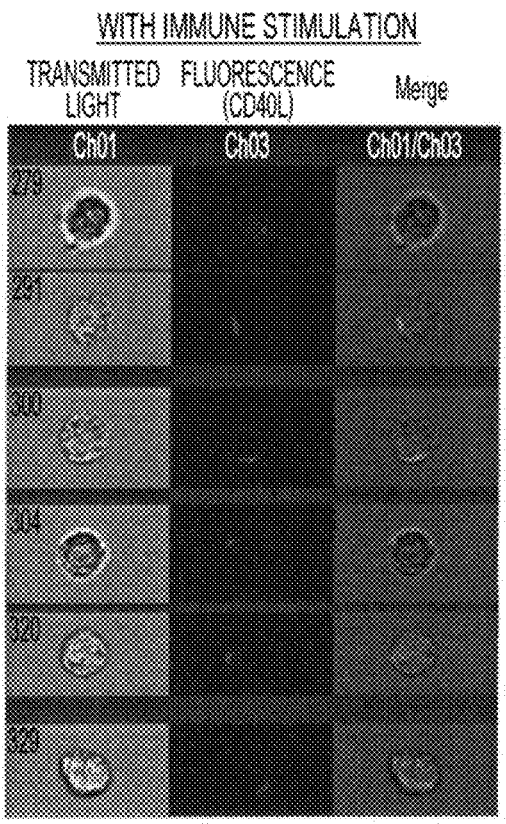
Figure 19B:
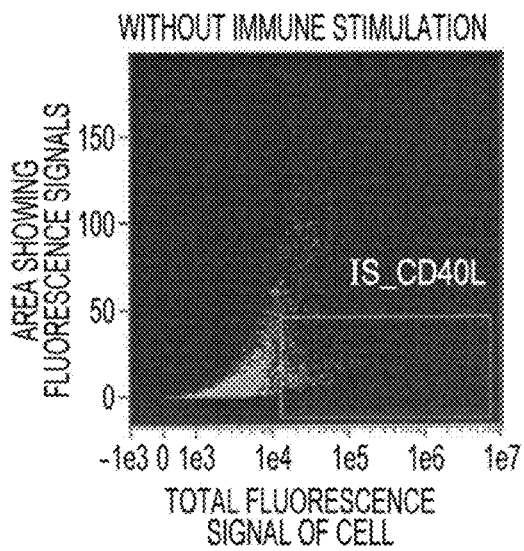
Figure 19D:
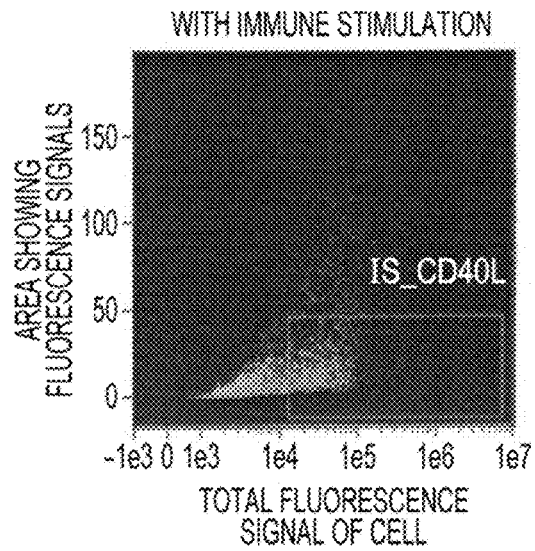

Data were plotted with the vertical axis as a proportion (%) of IFN-γ positive cells and the horizontal axis as a proportion (%) of immune synapse-forming cells. The resulting graph is shown in FIG. 16. As can be seen from FIG. 16, a correlation was observed between immune synapse formation and INF-γ production in immune-stimulated clonal T cells ($R^2$=0.8371). Accordingly, it was shown that immune cells activated by immune stimulation can be detected by detecting immune synapse in the immune cell from which the contact surface has been eliminated, similarly to the conventional method based on cytokine production.

Example 2: Measurement of Immunostimulatory Response of Immune Cells Using of CD3 and CD40 as Index (1) Stimulation and Measurement of Immune Cells In the same manner as in Example 1, the anti-CD3 antibody was immobilized on each well of the plate to prepare an anti-CD3 antibody-immobilized plate. Also, in the same manner as in Example 1, clonal T cells were prepared from human peripheral blood. The prepared clonal T cells were added to the anti-CD3 antibody-immobilized plate to give about $5 \times 10^5$ cells per well. Then, anti-CD28 antibody (BioLegend #302914 Clone: CD28.2) and PE labeled anti-CD40L antibody (BD biosciences #340477 Clone: 89-76) were added to the cells in the wells so as to have a final concentration of 0.01 mg/ml and 0.01 mg/ml, respectively. The plate was centrifuged (200 G, 60 seconds) and incubated at 37° C. for 30 minutes. After the supernatant in the wells was removed, the prepared clonal T cells were dispersed by pipetting and recovered from the well surface. The recovered T cells were immobilized using a fixing solution containing 1% PFA. The immobilized T cells were immunostained using APC-labeled anti-CD3 antibody (BioLegend #300411 Clone: UCHT1). The T cells were immunostimulated with PE-labeled anti-CD40L antibody, thus were in an immunostained state also with the anti-CD40L antibody. The stained T cells ($5 \times 10^5$ cells/20 µl) were measured using Imaging FCM (ImageStreamX Mark II Imaging Flow Cytometer: Amnis).

For comparison, the case where cells were not immunostimulated by contact with anti-CD40L antibody, anti-CD28 antibody and anti-CD3 antibody and contact with wells of plate was also examined. The clonal T cells prepared in the above (1) were fixed using the fixing solution described above on the ice, without performing the above-described immune stimulation. The fixed T cells were immunostained using APC-labeled anti-CD3 antibody and PE-labeled anti-CD40L antibody, and measured using Imaging FCM.

When the immune stimulation was not given to the prepared clonal T cells, both CD3 and CD40L were uniformly distributed on the cell membrane in the T cells (see FIGS. 17A and 17C, FIGS. 18A and 18B, and FIGS. 19A and 19B). When the immune stimulation was given and then the contact surface between the T cell and the well was eliminated, both CD3 and CD40L showed localization on the cell membrane of T cells (see FIGS. 17B and 17D, FIGS. 18C and 18D, FIGS. 19C and 19D). As described above, even when the immune stimulation was given and then the contact surface between the T cell and the well was eliminated, immune synapse could be detected by using CD3 or CD40L that is a surface antigen of the T cell as an index.

(2) Data Analysis

Figure 20A:
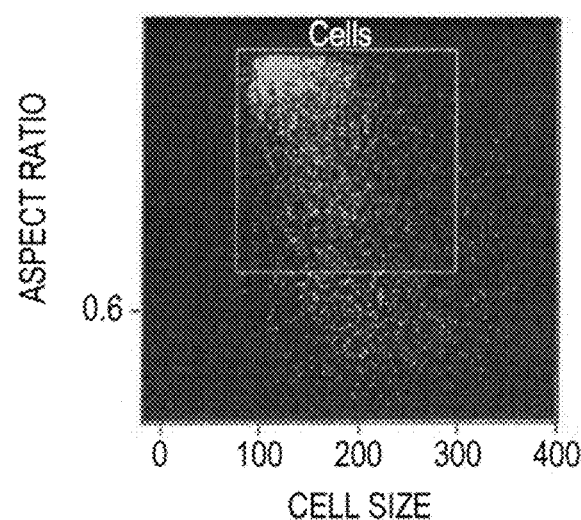
FIGS. 20A and 20B are 2D scattergrams showing an example of the measurement processing and analysis processing in Embodiment 2.
Figure 20B:
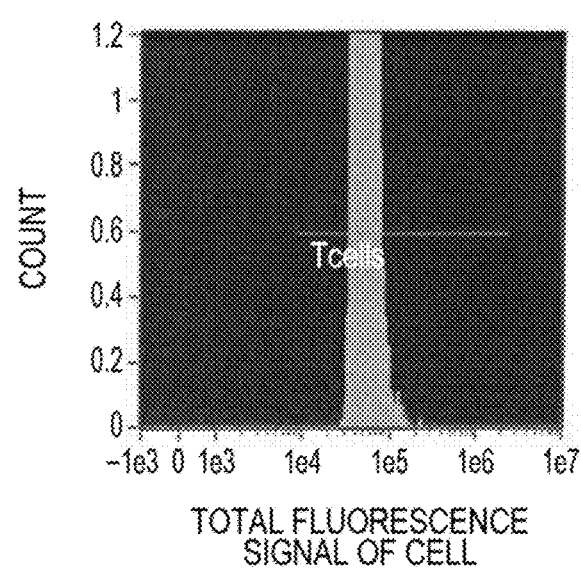
Figure 22A:
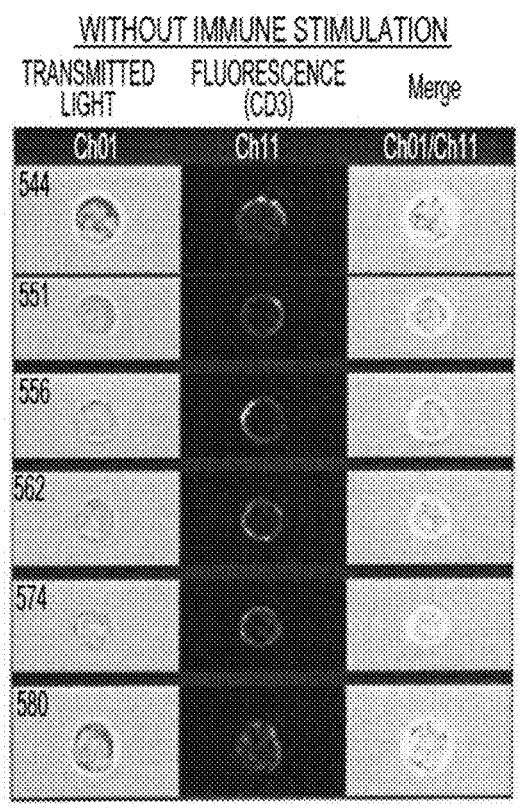
FIGS. 22A, 22B, 22C, and 22D are images and 2D scattergrams showing the distribution of CD3 in T cells. Transmitted light images, fluorescence images of T cells and superimposed images thereof (Merge) in the case without stimulation (FIG. 22A) and the case with stimulation (FIG. 22C). 2D scattergrams showing the total fluorescence signal intensity of the cell (X axis) and the area showing fluorescence signals (Y axis) in the case without stimulation (FIG. 22B) and the case with stimulation (FIG. 22D)
Figure 22C:
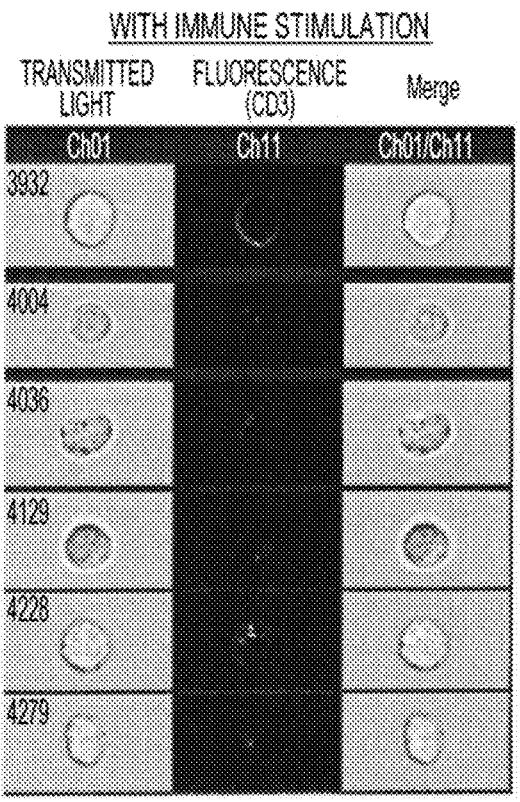
Figure 22B:
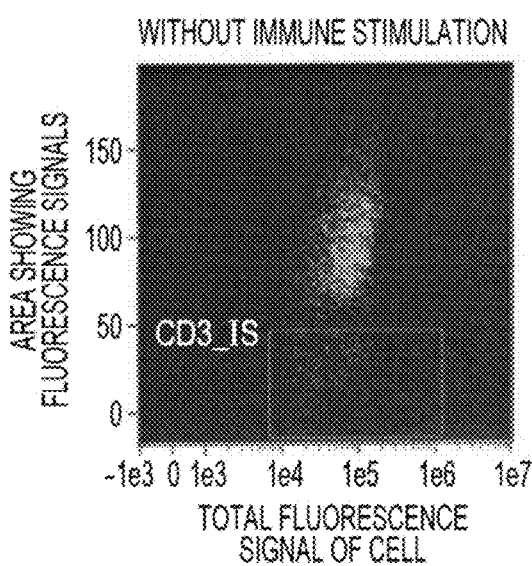
Figure 22D:
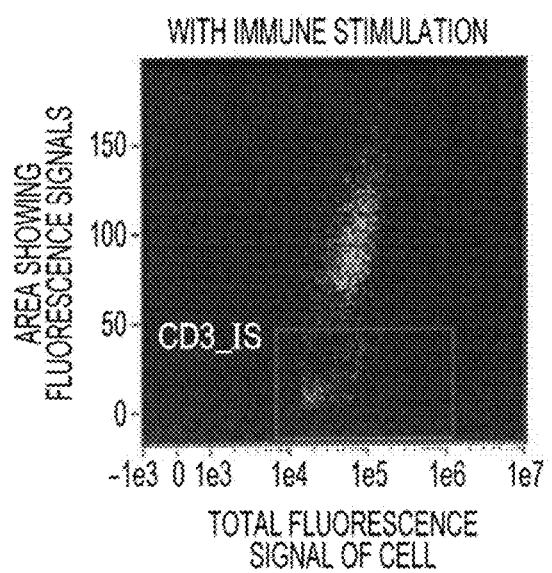
Figure 23A:
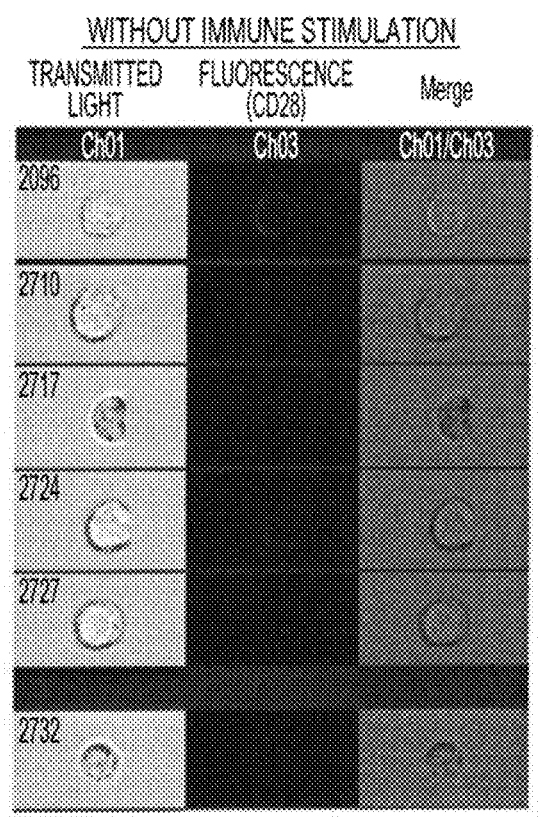
FIGS. 23A, 23B, 23C, and 23D are images and 2D scattergrams showing the distribution of CD28 in T cells. Transmitted light images, fluorescence images of T cells and superimposed images thereof (Merge) in the case without stimulation (FIG. 23A) and the case with stimulation (FIG. 23C). 2D scattergrams showing the total fluorescence signal intensity of the cell (X axis) and the area showing fluorescence signals (Y axis) in the case without stimulation (FIG. 23B) and the case with stimulation (FIG. 23D)
Figure 23C:
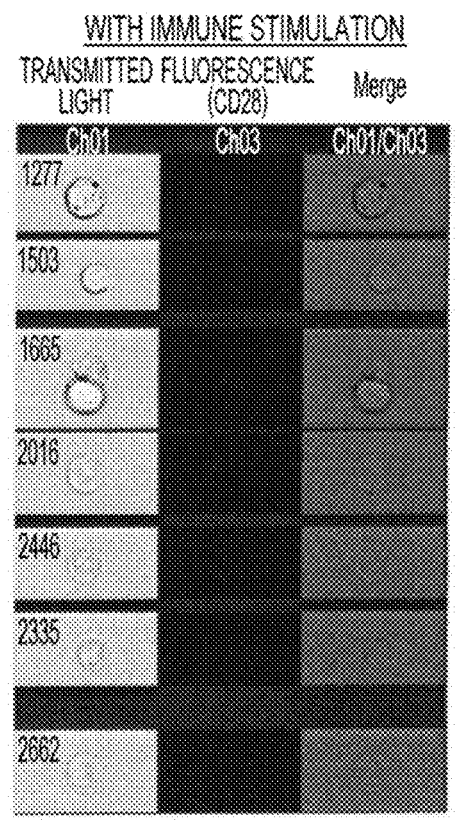
Figure 23B:
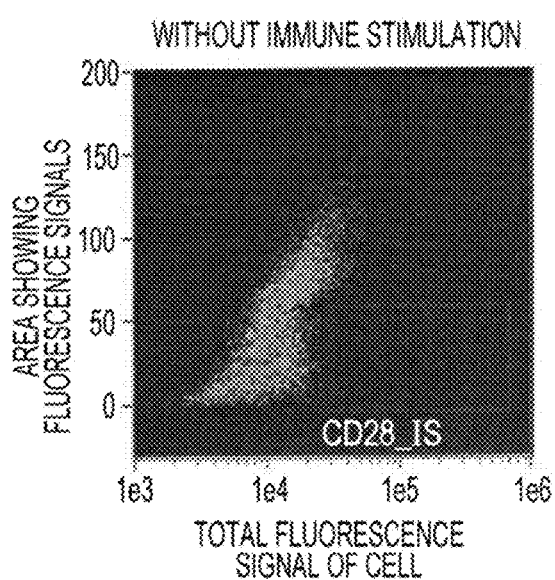
Figure 23D:
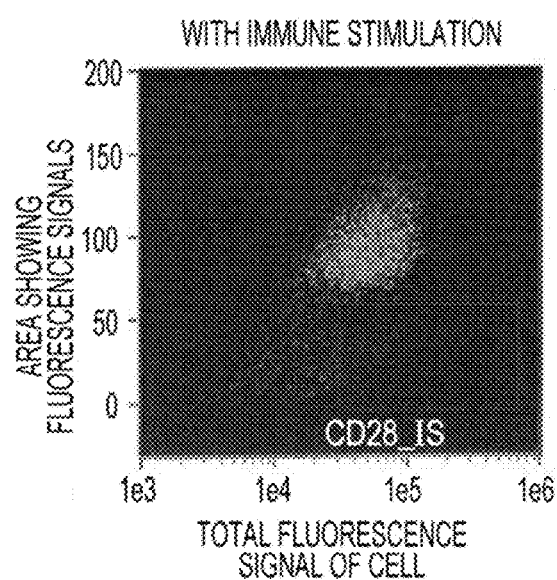
Figure 24A:
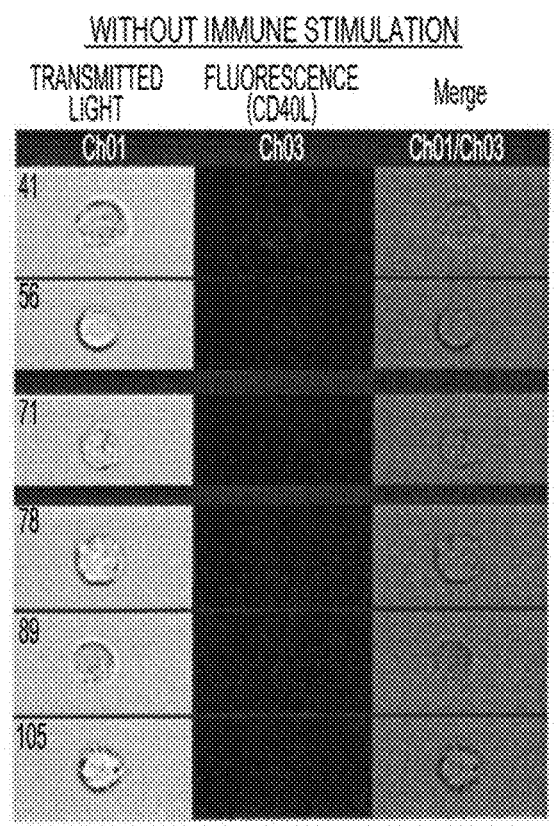
FIGS. 24A, 24B, 24C, and 24D are images and 2D scattergrams showing the distribution of CD40L in T cells. Transmitted light images, fluorescence images of T cells and superimposed images thereof (Merge) in the case without stimulation (FIG. 24A) and the case with stimulation (FIG. 24C). 2D scattergrams showing the total fluorescence signal intensity of the cell (X axis) and the area showing fluorescence signals (Y axis) in the case without stimulation (FIG. 24B) and the case with stimulation (FIG. 24D)
Figure 24C:
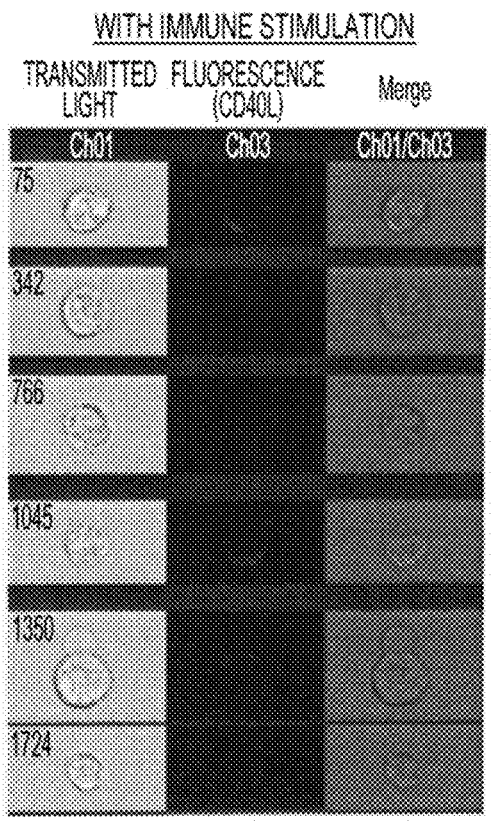
Figure 24B:
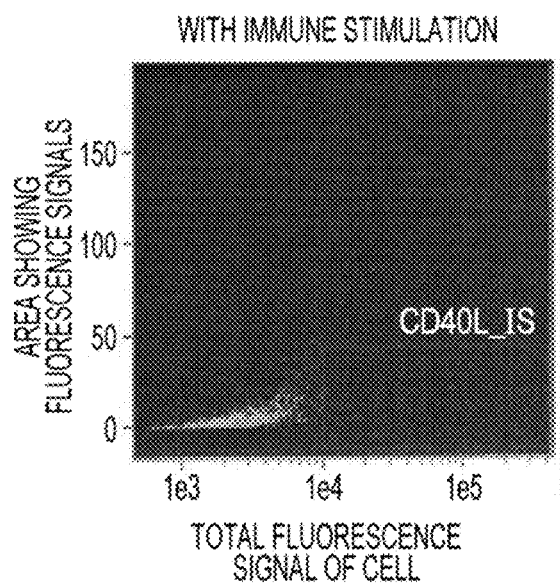
Figure 24D:
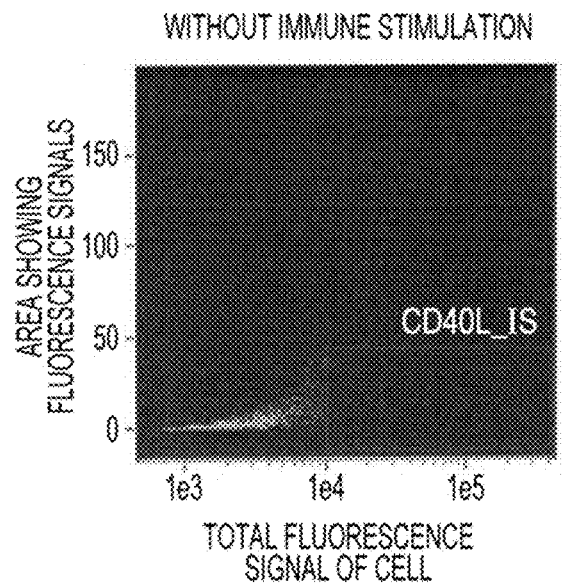
Figure 25A:
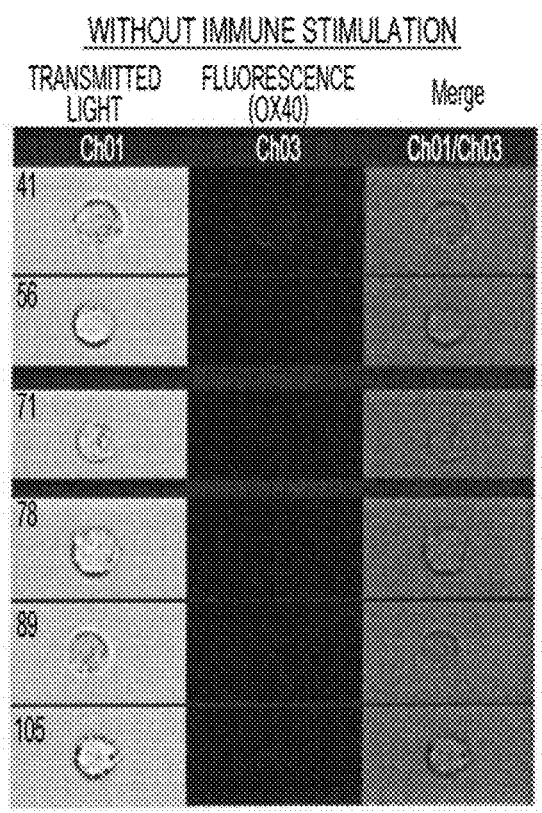
FIGS. 25A, 25B, 25C, and 25D are images and 2D scattergrams showing the distribution of OX40 in T cells. Transmitted light images, fluorescence images of T cells and superimposed images thereof (Merge) in the case without stimulation (FIG. 25A) and the case with stimulation (FIG. 25C). 2D scattergrams showing the total fluorescence signal intensity of the cell (X axis) and the area showing fluorescence signals (Y axis) in the case without stimulation (FIG. 25B) and the case with stimulation (FIG. 25D).
Figure 25C:
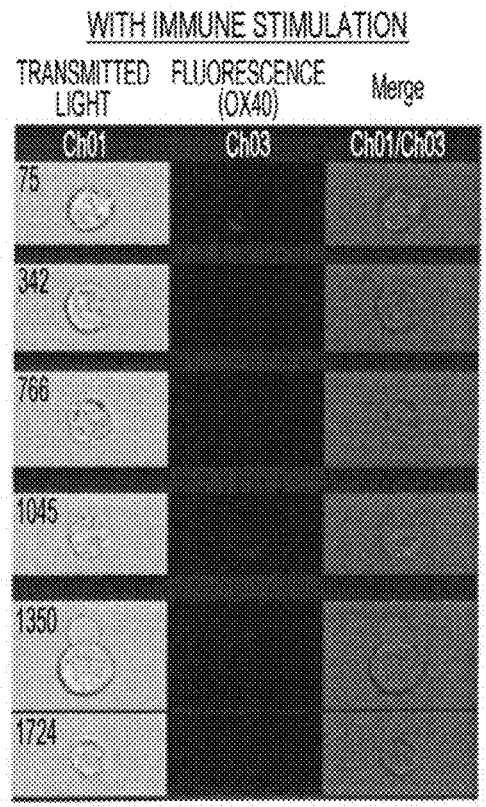
Figure 25B:
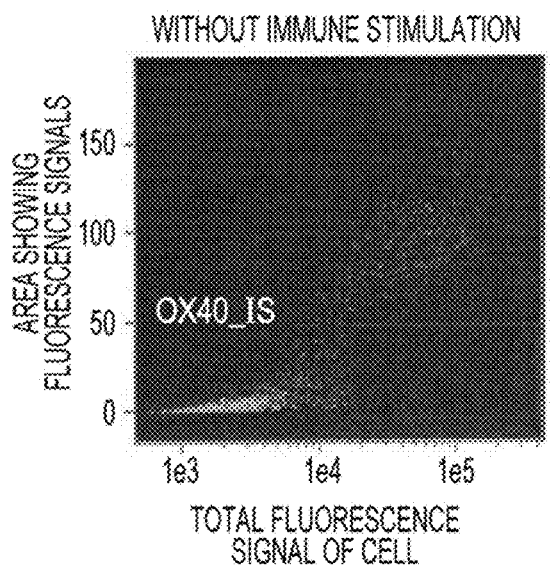
Figure 25D:
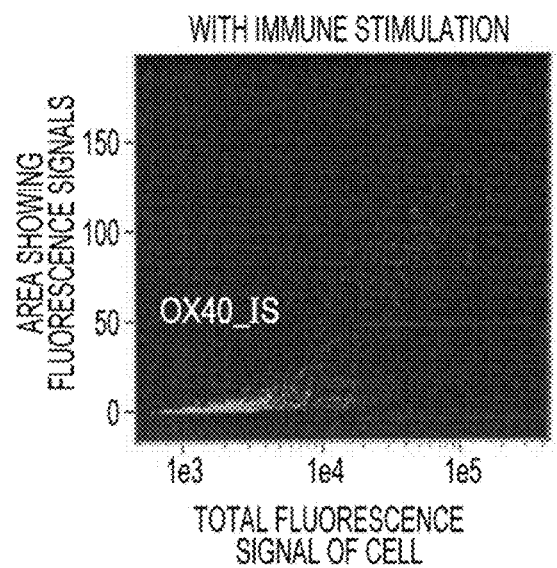

Multiple parameter analysis of the measurement data (FIGS. 18A and 18B) of the sample containing T cells without immune stimulation and the measurement data (FIGS. 18C and 18D) of the sample containing T cells with immune stimulation obtained by measurement using Imaging FCM was performed. An example of measurement processing and analysis processing in Embodiment 2 is shown in FIG. 20. Briefly, images were analyzed based on the transmitted light images and the fluorescence images (CD3 and CD40L) measured using Imaging FCM, and the cell size (the number of pixels), the cell aspect ratio, the area (the number of pixels) showing the fluorescence signals in the cell and the total fluorescence signal intensity (total fluorescence signal intensity of the cell) within the area were measured. First, a 2D scattergram (see FIG. 20A) in which the cell size was assigned to the X axis and the cell aspect ratio was assigned to the Y axis was generated, and the measurement data of the cells corresponding to dots in the predetermined range (Cells) was extracted. Next, for the measurement data in the range (Cells), the measurement data corresponding to dots in which the total fluorescence signal intensity of the cell is in the predetermined range (Tcells) was further extracted (see FIG. 20B). For the measurement data in the range (Tcells), the numbers of dots in the regions displayed as IS_CD3 and IS_CD40L (see FIGS. 18C and 18D, and FIGS. 19C and 19D) were counted, respectively. Also, the numbers of dots on the scattergrams of FIGS. 18C and 18D, FIGS. 19C and 19D (the number of dots in the range (Tcells)) were counted. Then, the ratios of the number of dots in the range (IS_CD3 or IS_CD40L) to the number of dots in the range (Tcells) were calculated by the following equation (2). The results are shown in Tables 2 and 3 below. IS is an abbreviation for Immune Synapse.

[Proportion (IS forming cells/Tcells)]={[Number of dots in range(IS_*CD*3 or IS_*CD*40*L*)]/[Number of dots in range(*T*cells)]}×100       (2)

TABLE 2

| | CD3 | |
|---|---|---|
| Analysis data | Without immune stimulation | With immune stimulation |
| T cells [count] | 7269 | 4481 |
| IS Forming cells [count] | 750 | 795 |
| Proportion(IS Forming cells/T cells) [%] | 10.32 | 17.74 |

TABLE 3

| | CD40L | |
|---|---|---|
| Analysis data | Without immune stimulation | With immune stimulation |
| T cells [count] | 7269 | 4481 |
| IS Forming cells [count] | 292 | 1463 |
| Proportion (IS forming cells/T cells) [%] | 4.02 | 32.65 |

As shown in Tables 2 and 3, it was shown that the proportion of T cells that formed immune synapse is clearly higher in the T cells stimulated with immunostimulatory antibodies than in the case of not immunostimulating the T cells. Accordingly, it was shown that the response of immune cells to immune stimulation by immunostimulatory antibodies can be measured, by detection of immune synapse using CD3 or CD40L as an index.

Example 3: Measurement of Immune Cells Responding to Immune Stimulation by Allogenic Cells (1) Allogenic Cells and Clonal T Cells Retinal pigment epithelial cells (RPE cells) prepared from iPS cells derived from a predetermined donor (allogenic iPS cells) were used as the allogenic cells. RPE cells were provided by HEALIOS K.K. RPE cells were seeded in 24-well plate to give about $5 \times 10^5$ cells per well and incubated at 37° C., 5% $CO_2$ for 7 days. Thereby, a plate having RPE cells adhered to the bottom surface of the well was obtained. Clonal T cells were prepared in the following method. $5 \times 10^6$ CD4 positive cells (Stemcell Technologies: ST-70026) and CD8 positive cells (Funakoshi: 0508-100, COSMO BIO: PB08C-1) were seeded in Yssel's medium (Gemini Bio-Products: 400102) added with 1 μg/mL LEAF (trademark) Purified anti-human CD3 Antibody (Biolegend: 317315), 10 ng/mL of Recombinant human IL-2 (rhIL-2) (R&D systems: 202-IL-500), 0.2 μg/mL of Phytohemagglutinin-L (PHA) (SIGMA: L4144-5 MG) and 2% human serum (SIGMA: H4522-100ML), and co-cultured with $1.2 \times 10^5$ RPE cells for 14 days.

Fourteen days later, T cells were seeded in 96-well plates so as to be 0.3, 1.0 and 3.0 cells/well by limiting dilution, and cultured until colonies with $1 \times 10^4$ RPE cells were formed. The T cells were recovered from the colonized wells to obtain clonal T cells.

(2) Stimulation and Measurement of Immune Cells

The prepared clonal T cells were added to a plate seeded with RPE cells to give about $5 \times 10^5$ cells per well. The plate was centrifuged (200 G, 120 seconds) and incubated at 37° C. for 30 minutes. After the supernatant in the wells was removed, the prepared clonal T cells were dispersed by pipetting and recovered from the well surface. The recovered T cells were immobilized using a fixing solution containing 1% PFA. The immobilized T cells were immunostained using APC-labeled anti-CD3 antibody (BioLegend #300411 Clone: UCHT1), anti-CD28 antibody (BioLegend #302914 Clone: CD28.2), PE labeled anti-CD40L antibody (BD biosciences #340477 Clone: 89-76) or PE labeled anti-OX40 antibody (BioLegend #350003 Clone: Ber-ACT35). The T cells immunostained with anti-CD28 antibody were further immunostained using PE-labeled anti-mouse IgG antibody (BioLegend #405307). The stained T cells ($5 \times 10^5$ cells/20 μl) were measured using Imaging FCM (ImageStreamX Mark II Imaging Flow Cytometer: Amnis).

For comparison, the cases where cells were not immunostimulated by contact with allogenic cells were also examined. The clonal T cells prepared in the above (1) were fixed using the fixing solution described above on the ice, without contacting with allogenic cells. The fixed T cells were immunostained using APC-labeled anti-CD3 antibody, anti-CD28 antibody, PE-labeled anti-CD40L antibody or PE-labeled anti-OX40 antibody, and measured using Imaging FCM.

When the immune stimulation by contact with allogenic cell was not given to the prepared clonal T cells, any of CD3, CD28, CD40L and OX40 were uniformly distributed on the cell membrane in the T cells (see FIGS. 21A, 21C, 21E and 21G, FIGS. 22A and 22B, FIGS. 23A and 23B, FIGS. 24A and 24B, and FIGS. 25A and 25B). When the immune stimulation was given and then the contact surface between the T cell and allogenic cell was eliminated, CD3, CD28, CD40L and OX40 showed localization on the cell membrane of T cells (see FIGS. 21B, 21D, 21F and 21H, FIGS. 22C and 22D, FIGS. 23C and 23D, FIGS. 24C and 24D, and FIGS. 25C and 25D). As described above, even when the immune stimulation by contact with allogenic cell was given and then the contact surface between the T cell and the allogenic cell was eliminated, immune synapse could be detected by using CD3, CD28, CD40L or OX40 that is a surface antigen of the T cell as an index.

(3) Data Analysis

Multiple parameter analysis of the measurement data (FIGS. 18A and 18B) of the sample containing T cells without immune stimulation and the measurement data (FIGS. 18C and 18D) of the sample containing T cells with immune stimulation obtained by measurement using Imaging FCM was performed. The measurement processing and analysis processing are the same as in Example 2. Briefly, images were analyzed based on the transmitted light image and the fluorescence image (CD3, CD28, CD40L or OX40) measured using Imaging FCM, and the cell size (the number of pixels), the cell aspect ratio, the area (the number of pixels) showing the fluorescence signals in the cell and the total fluorescence signal intensity (total fluorescence signal intensity of the cell) within the area were measured. First, a 2D scattergram in which the cell size was assigned to the X axis and the cell aspect ratio was assigned to the Y axis was generated, and the measurement data of the cells corresponding to dots in the predetermined range (Cells) was extracted. Next, for the measurement data in the range (Cells), the measurement data corresponding to dots in which the total fluorescence signal intensity of the cell is in the predetermined range (Tcells) was further extracted. For the measurement data in the range (Tcells), the numbers of dots in the regions displayed as IS_CD3, IS_CD28, IS_CD40L and IS_OX40 (see FIGS. 22B and 22D, FIGS. 23B and 23D, FIGS. 24B and 24D and FIGS. 25B and 25D) were counted, respectively. Also, the number of dots on each scattergram (the number of dots in the range (Tcells)) was counted. Then, the ratios of the number of dots in the ranges (IS_CD3, IS_CD28, IS_CD40L and IS_OX40) to the number of dots in the range (Tcells) were calculated by the following equation (3). The results are shown in Tables 4 to 7 below.

[Proportion (IS forming cells/Tcells)]={[Number of dots in range(IS_CD3,IS_CD28,IS_CD40L or IS_OX40)]/[Number of dots in range(Tcells)]}× 100 (3)

TABLE 4

| | CD3 | |
| --- | --- | --- |
| Analysis data | Without immune stimulation | With immune stimulation |
| T cells [count] | 2758 | 1905 |
| IS Forming cells [count] | 161 | 471 |
| Proportion (IS forming cells/T cells) [%] | 5.84 | 24.72 |

TABLE 5

| | CD28 | |
| --- | --- | --- |
| Analysis data | Without immune stimulation | With immune stimulation |
| T cells [count] | 2758 | 1881 |
| IS Forming cells [count] | 75 | 114 |
| Proportion (IS forming cells/T cells) [%] | 2.72 | 6.06 |

TABLE 6

CD40L

| Analysis data | Without immune stimulation | With immune stimulation |
|---|---|---|
| T cells [count] | 1872 | 1052 |
| IS Forming cells [count] | 46 | 64 |
| Proportion (IS forming cells/T cells) [%] | 2.46 | 6.08 |

TABLE 7

OX40

| Analysis data | Without immune stimulation | With immune stimulation |
|---|---|---|
| T cells [count] | 2758 | 1881 |
| IS Forming cells [count] | 75 | 114 |
| Proportion (IS forming cells/T cells) [%] | 2.72 | 6.06 |

As shown in Tables 4 to 7, it was shown that the proportion of T cells that formed immune synapse is clearly higher in the T cells immunostimulated with allogenic cells than in the case of not immunostimulating the T cells. Accordingly, it was shown that the response of immune cells to immune stimulation by allogenic cells can be measured, by detection of immune synapse using CD3, CD28, CD40L or OX40 as an index.

What is claimed is:

1. A method for determining an immunostimulatory response of an immune cell, comprising:
   (i) contacting a measurement target immune cell, an immunostimulator, and a substance different from the measurement target immune cell;
   (ii) separating the measurement target immune cell and the substance different from the measurement target immune cell, and labeling a molecule which is a component of an immune synapse of the measurement target immune cell with a fluorescent substance, whereby the measurement target immune cell to which the fluorescent substance is bound is prepared;
   (iii) detecting a fluorescence generated from the fluorescent substance bound to the measurement target immune cell; and
   (iv) determining the immunostimulatory response of the measurement target immune cell based on the fluorescence detected in step (iii).

2. The method according to claim 1, wherein the immunostimulator is present on the substance different from the measurement target immune cell.

3. The method according to claim 1, further comprising fractionating the measurement target immune cell from a sample containing cells, based on cell size, aggregation degree and/or specific gravity.

4. The method according to claim 1, wherein the molecule which is a component of the immune synapse is at least one selected from the group consisting of T cell receptor α/β (TCRα/β) CD3, CD40L, OX40, CD28, Cytotoxic T-lymphocyte-associated protein 4 (CTLA4), Programmed cell death protein 1 (PD-1) and Inducible T-cell COStimulator (ICOS).

5. The method according to claim 1, wherein the molecule which is a component of the immune synapse is a costimulatory molecule.

6. The method according to claim 1, wherein the fluorescent substance comprises a substance capable of generating a fluorescent signal, linked to an antibody, an antibody fragment, a single chain antibody, or an aptamer.

7. The method according to claim 1, wherein the immunostimulator comprises at least one of an immunostimulatory antibody, an immunostimulatory peptide, a major histocompatibility molecule (WIC molecule), and a complex of an WIC molecule and an antigenic peptide.

8. The method according to claim 7, wherein the immunostimulatory antibody is an antibody that specifically binds to a co-stimulatory molecule on the target measurement immune cell.

9. The method according to claim 8, wherein the immunostimulatory antibody is at least one selected from the group consisting of an anti-TCR α/β antibody, an anti-CD3 antibody, an anti-CD40L antibody, an anti-0X40 antibody, an anti-CD2 antibody, an anti-CD28 antibody, an anti-CD137 antibody, an anti-CTLA4 antibody, an anti-PD-1 antibody, an anti-ICOS antibody, and an anti-integrin antibody.

10. The method according to claim 1, wherein the substance different from the measurement target immune cell is an allogenic cell, an antigen-presenting cell, a cancer cell, a container, a multi-well plate, a slide, or a bead.

11. The method according to claim 1, wherein the measurement target immune cell is a T cell.

12. The method according to claim 1, wherein, in the step (iv), a value reflecting a distribution of the molecule which is a component of the immune synapse is measured, based on the detected fluorescent signal, and the measured value is compared with a threshold value, thereby determining whether or not the measurement target immune cell has an immunostimulatory response.

13. The method according to claim 12, wherein said method further comprises:
    acquiring a fluorescence image based on the detected fluorescence signal;
    measuring, in said fluorescence image, an area showing fluorescence signals that reflects the distribution of the molecule which is a component of the immune synapse; and
    comparing the measured area with a threshold value, thereby determining whether or not the measurement target immune cell has an immunostimulatory response.

14. The method according to claim 13, wherein when the measured area is smaller than the threshold value, the measurement target immune cell is determined to have the immunostimulatory response.

15. The method according to claim 1, wherein, when the substance different from the measurement target immune cell is an allogenic cell, an antigen-presenting cell, a cancer cell or a bead, the detecting of step (iii) is performed using a flow cytometer or an imaging cytometer, on a complex of the measurement target immune cell, the substance different from the measurement target immune cell, and the fluorescent substance;

or when the substance different from the measurement target immune cell is a container, a multi-well plate or a slide, the detecting of step (iii) is performed using a flow cytometer or an imaging cytometer, on a complex of the measurement target immune cell and the fluorescent substance, wherein the complex does not contain the substance different from the measurement target immune cell.

16. The method according to claim 1, wherein the substance different from the measurement target immune cell is a cell other than the measurement target immune cell.

17. The method according to claim 1, wherein in the labeling step, the immunostimulator which is bound to the measurement target immune cell is labeled with an antibody which comprises the fluorescent substance.

18. A method for determining the formation of an immune synapse, comprising:
  (i) contacting a measurement target immune cell, an immunostimulator, and a substance different from the measurement target immune cell;
  (ii) separating the measurement target immune cell and the substance different from the measurement target immune cell, and binding a capturing body to the immunostimulator which is bound to the measurement target immune cell, the capturing body specifically binding to the immunostimulator and comprising a fluorescent substance, whereby a molecule which is a component of an immune synapse of the measurement target immune cell is labeled with a fluorescent substance, and the measurement target immune cell to which the fluorescent substance is bound is prepared;
  (iii) detecting a fluorescence generated from the fluorescent substance bound to the measurement target immune cell; and
  (iv) determining whether an immune synapse is formed on the measurement target immune cell based on the fluorescence detected in the step of (iii).

19. A method for determining an immunostimulatory response of an immune cell, comprising:
  (i) stimulating a measurement target immune cell with an immunostimulator and contacting the measurement target immune cell with a substance different from the measurement target immune cell;
  (ii) separating the measurement target immune cell from the substance different from the measurement target immune cell, and labeling a contact surface on the measurement target immune cell with a fluorescent substance;
  (iii) detecting a fluorescence generated from the fluorescent substance bound to the measurement target immune cell; and
  (iv) determining the immunostimulatory response of the measurement target immune cell based on the fluorescence detected in the step of (iii).

* * * * *